United States Patent [19]
Konishi

[11] Patent Number: 5,657,110
[45] Date of Patent: Aug. 12, 1997

[54] METHOD OF DETECTING EYE COMPONENT INFORMATION FOR DETERMINING SIGHT AXIS DIRECTION, AND SIGHT AXIS DIRECTION DETECTION APPARATUS

[75] Inventor: Kazuki Konishi, Tokyo, Japan

[73] Assignee: Canon Kabushiki Kaisha, Tokyo, Japan

[21] Appl. No.: 431,300

[22] Filed: Apr. 28, 1995

Related U.S. Application Data

[62] Division of Ser. No. 45,194, Apr. 13, 1993, Pat. No. 5,469,234.

[30] Foreign Application Priority Data

Apr. 14, 1992 [JP] Japan .................. 4-120062

[51] Int. Cl.$^6$ .................................................. A61B 3/10
[52] U.S. Cl. ..................... 351/212; 351/211; 351/247
[58] Field of Search ............................. 351/211, 212, 351/209, 210, 246, 247, 205, 206; 354/62

[56] References Cited

U.S. PATENT DOCUMENTS

| | | | |
|---|---|---|---|
| 4,836,670 | 6/1989 | Hutchinson | 351/210 |
| 5,036,347 | 7/1991 | Tsunekawa et al. | 354/62 |
| 5,280,312 | 1/1994 | Yamada et al. | 351/211 |
| 5,298,927 | 3/1994 | Konishi et al. | 351/210 |

FOREIGN PATENT DOCUMENTS

| | | |
|---|---|---|
| 61-172552 | 8/1986 | Japan . |
| 3-109030 | 5/1991 | Japan . |

*Primary Examiner*—Hung X. Dang
*Attorney, Agent, or Firm*—Fitzpatrick, Cella, Harper & Scinto

[57] ABSTRACT

In a pupil center detection method and a pupil ring portion detection method, which can obtain a pupil center and a pupil ring portion necessary for calculating a sight axis of an eyeball from specific points on the basis of a light beam reflected by the eyeball, when the position of the pupil center of the eyeball is detected by utilizing an image based on a light beam radiated from a projection device onto the eyeball and reflected by the eyeball, a large number of pupil ring portion positions are obtained, an average value and a standard deviation of the large number of pupil ring portion positions are obtained, and the pupil center is detected using values within a range defined by the average value and the standard deviation.

8 Claims, 21 Drawing Sheets

TO FIG.7

PATTERN OF IRIS

SIGNAL VARIATION BY NON-UNIFORM LIGHT PROJECTION

METHOD OF DETECTING EYE COMPONENT INFORMATION FOR DETERMINING SIGHT AXIS DIRECTION, AND SIGHT AXIS DIRECTION DETECTION APPARATUS

This application is a division of application Ser. No. 08/045,194 filed Apr. 13, 1993, now U.S. Pat. No. 5,469,234.

BACKGROUND OF THE INVENTION

1. Field of the Invention

The present invention relates to a pupil center detection method, a pupil ring detection method, and an apparatus adopting these methods and, more particularly, to a method and apparatus suitably used in a case wherein a light beam is radiated from a projection means onto an eyeball of an observer (photographer), a first Purkinje image (a cornea reflecting image) and a pupil image based on light reflected by the eyeball are formed on an image sensor surface, and the sight axis of the eyeball is detected using the position coordinates of these images on the image sensor surface.

2. Related Background Art

Conventionally, there have been proposed various sight axis detection apparatuses for detecting the observation position of an observer (photographer) on an observation surface, i.e., detecting a so-called sight axis of the observer.

For example, in Japanese Laid-Open Patent Application No. 61-172552, a parallel light beam from a light source is projected onto a front eye part of an eye to be detected, and the sight axis (view point) is obtained by utilizing a cornea reflecting image based on light reflected by a cornea and a focusing state at a position of the pupil center.

FIG. 18 is an explanatory view of a sight axis detection method according to an embodiment proposed by the above patent. FIGS. 19A and 19B are respectively a front view of an eyeball shown in FIG. 18, and a chart showing an output signal from a line sensor shown in FIG. 18.

In FIG. 18, a light source 704 such as a light-emitting diode for emitting infrared light unsensible by an observer is arranged on a focal plane of a projection lens 706. Infrared light emitted from the light source 704 is collimated into parallel light by the projection lens 706, is reflected by a half mirror 710, and illuminates a cornea 701 of an eyeball 700. At this time, some light components (cornea reflecting image or Purkinje image) of the infrared light reflected by the surface of the cornea 701 are transmitted through the half mirror 710, are converged by a light-receiving lens 707, and form an image at a position d' on an image sensor 709.

On the other hand, light beams reflected by edge portions (pupil ring portions) a and b of an iris 703 are guided onto the image sensor 709 via the half mirror 710 and the light-receiving lens 707, and form images of the edge portions (pupil ring portions) a and b at positions a' and b' on the image sensor 709. When a rotational angle θ of an optical axis T of the eyeball with respect to an optical axis S of the light-receiving lens 707 is small, if the z-coordinates of the edge portions a and b of the iris 703 are represented by Za and Zb, a coordinate Zc of a central position (pupil center) position c of the iris 703 is given by:

$$Zc \simeq \frac{Za + Zb}{2}$$

If the z-coordinate of the generation position d of the cornea reflection image is represented by Zd, and the distance between the center O of curvature of the cornea 701 and the center C of the iris 703 is represented by LOC, the rotational angle θ of the optical axis T of the eyeball substantially satisfies:

$$LOC \cdot \sin \theta \simeq Zc - Zd \quad (1)$$

For this reason, the rotational angle θ of the optical axis T of the eyeball is obtained by detecting the positions of specific points (images Zd', Za', and Zb', on the image sensor 709, of the generation position d of the cornea reflecting image and edge portions a and b of the iris) projected onto the image sensor 709, thereby obtaining the sight axis of the observer. At this time, relation (1) can be rewritten as:

$$\beta \cdot LOC \cdot \sin\theta \simeq \frac{Za' + Zb'}{2} - Zd' \quad (2)$$

where β is the magnification determined by a distance L between the generation position d of the cornea reflecting image and the light-receiving lens 707, and a distance $L_0$ between the light-receiving lens 707 and the image sensor 709, and normally assumes an almost constant value.

As described above, when the sight axis direction (view point) of the eye to be detected of the observer is detected, the observation position on the focusing screen can be known in, e.g., a single-lens reflex camera.

FIG. 19B shows the brightness distribution of an image on a 1-line sensor array 709a of the image sensor 709. Since the iris 703 has a higher reflectance than that of a pupil 711, the image of the iris 703 becomes brighter than that of the pupil 711. In FIG. 19B, points Ra and Rb where the brightness largely changes correspond to two points a' and b' where the boundaries between the pupil 711 and the iris 703 cross the sensor array 709a.

Note that Rc is an output corresponding to a Purkinje effect image. For example, digital data converted by an A/D converter in units of pixels are checked from the two ends of the sensor array 709a to obtain points where the output changes from bright level La to dark level Lb for the first time, thus obtaining the two points a' and b' where boundaries a and b between the pupil 711 and the iris 703 cross the sensor array 709a. From these two crossing points a' and b', the pupil center can be obtained by averaging the pupil ring portions a and b and the two points a' and b'.

SUMMARY OF THE INVENTION

A signal waveform obtained from the sensor array 709a of the image sensor 709 (FIG. 18) varies, as shown in, e.g., FIGS. 20 to 23, under the influence of various noise components. In FIGS. 20 to 23, the coordinates of the sensor array are plotted along the abscissa.

For this reason, it is difficult for the conventional method of simply obtaining points where the output changes from bright level to dark level for the first time to precisely extract the pupil center and the pupil ring portions.

A Purkinje image may often be located outside the pupil or the pupil may be eclipsed by an eyelid. In this case, the first change point from bright level to dark level does not correspond to each pupil ring portion, and it is difficult for the conventional method to calculate the pupil center and the pupil ring portions.

Since it is difficult for the conventional method to detect the pupil center and the pupil ring, it is very hard to detect the sight axis of the eyeball with high precision.

A method utilizing a pupil ring for sight axis detection is known in U.S. Pat. No. 4,836,670.

It is an object of the present invention to detect a pupil center and pupil ring portions, i.e., the sight axis of an eyeball with high precision by properly processing signals obtained from an image sensor on the basis of specific points based on light beams reflected by the eyeball.

It is another object of the present invention to, when the position of a pupil center of an eyeball is detected by utilizing an image based on a light beam radiated from a projection means onto the eyeball and reflected by the eyeball, obtain a large number of positions on a pupil ring portion, calculate an average value and a standard deviation of the plurality of positions on the pupil ring portion, and detect the pupil center using values within a range defined by the average value and the standard deviation.

It is still another object of the present invention to, when the position of a pupil center of an eyeball is detected by utilizing an image based on a light beam radiated from projection means onto the eyeball, and reflected by the eyeball, detect the pupil center of the eyeball based on an average value of a pair of positions on a pupil ring portion detected on a single line in each of the horizontal and vertical directions with respect to the eyeball.

It is still another object of the present invention to, when the position of a pupil center of an eyeball is detected by utilizing an image based on a light beam radiated from projection means onto an eyeball, and reflected by the eyeball, obtain a large number of pupil central positions in the horizontal and vertical directions with respect to the eyeball, calculate an average value and a standard deviation of the large number of pupil central positions, and detect the pupil center using a value within a range defined by these values.

It is still another object of the present invention to, when the position of a pupil center of an eyeball is detected by utilizing an image based on a light be radiated from projection means onto the eyeball, and reflected by the eyeball, obtain a large number of positions on a pupil ring, presume a pupil central position and a pupil diameter using the information of the large number of positions on the pupil ring, and detect the pupil center using a value within a range determined by the presumed pupil central position and pupil diameter.

It is still another object of the present invention to, when an image based on a light beam radiated from projection means onto an eyeball and reflected by the eyeball is detected by detection means consisting of a plurality of sensors, and the position of a pupil ring of the eyeball is detected by utilizing the output signals from the detection means, detect a position where the output signals from the sensors continuously increase or decrease over several pixels or more as the position of the pupil ring.

It is still another object of the present invention to, when an image based on a light beam radiated from projection means onto an eyeball, and reflected by the eyeball is detected by detection means consisting of a plurality of sensors, and the position of a pupil ring of the eyeball is detected by utilizing the output signals from the detection means, detect a minimum value of the output signals from the sensors, and to, when the start point of a portion where the output signals from the sensors continuously increase over several pixels or more and the end point of a portion where the output signals from the sensors continuously decrease over several pixels or more are substantially equal to the minimum value, detect the positions where the output signals increase and decrease as the pupil ring.

It is still another object of the present invention to, when an image based on a light beam radiated from projection means onto an eyeball, and reflected by the eyeball is detected by detection means consisting of a plurality of sensors, and the position of a pupil ring of the eyeball is detected by utilizing the output signals from the detection means, detect maximum and minimum values of the output signals from the sensors, and to, when the end point of a portion where the output signals from the sensors continuously increase over several pixels or more and the end point of a portion where the output signals from the sensors continuously decrease over several pixels or more are smaller than an average value of the maximum and minimum value, detect the positions where the output signals increase and decrease as the pupil ring.

It is still another object of the present invention to, when a Purkinje image based on a light beam radiated from projection means onto an eyeball, and reflected by the eyeball is detected by detection means consisting of a plurality of sensors, and the position of a pupil ring of the eyeball is detected using the output signals from the detection means, detect the position of the Purkinje image, and to, when both the start and end points of a portion where the output signals from the sensors continuously increase over several pixels or more are not present near the Purkinje image, and the start and end points of a portion where the output signals from the sensors continuously decrease over several pixels or more are not present near the Purkinje image, detect the positions where the output signals increase and decrease as the positions of the pupil ring.

It is still another object of the present invention to, when the position of a pupil ring of an eyeball is detected by utilizing an image based on a light beam radiated from projection means onto the eyeball, and reflected by the eyeball, perform the same signal processing and calculations for output signals in the horizontal and vertical directions with respect to the eyeball, thereby calculating the position of the pupil ring.

It is still another object of the present invention to, when the position of a pupil ring of an eyeball is detected by utilizing a Purkinje image based on a light beam radiated from projection means onto the eyeball, and reflected by the eyeball, determine the start point of a detection calculation of the position of the pupil ring on the basis of the detection result of the position of the Purkinje image.

It is still another object of the present invention to determine the start point of a detection calculation of the pupil ring as an average value or one of positions of a plurality of Purkinje images.

It is still another object of the present invention to, when an image based on a light beam radiated from projection means onto an eyeball and reflected by the eyeball is detected by detection means, and the position of a pupil ring of the eyeball is detected by utilizing signals from the detection means, presume a minimum luminance portion from all signals obtained by the detection means, and start a detection calculation of the position of the pupil ring from the presumed portion.

BRIEF DESCRIPTION OF THE ATTACHED DRAWINGS

DESCRIPTION OF THE PREFERRED EMBODIMENTS

Figure 1:
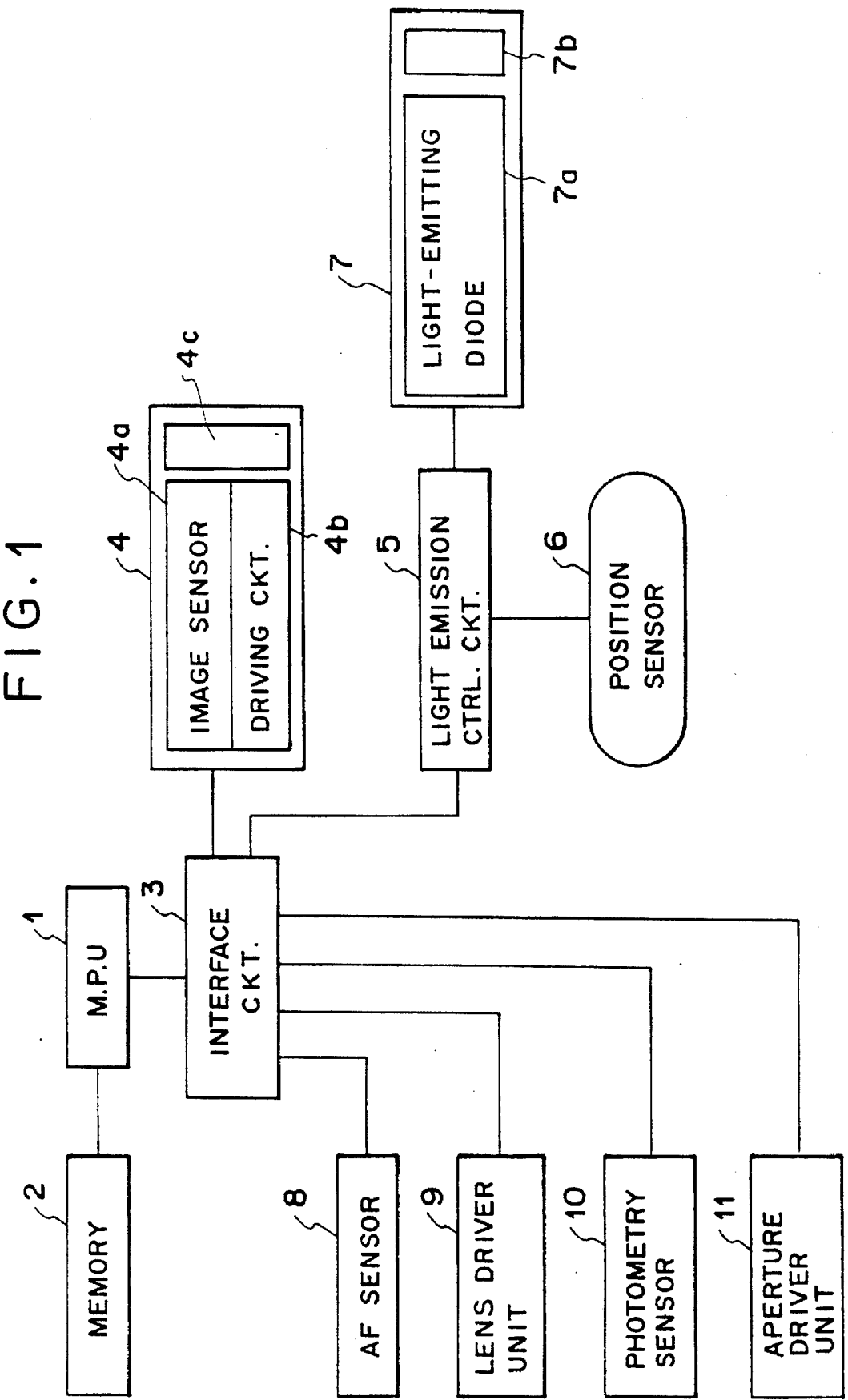
FIG. 1 is a block diagram showing, a main part when the present invention is applied to a single-lens reflex camera.
Figure 2A:
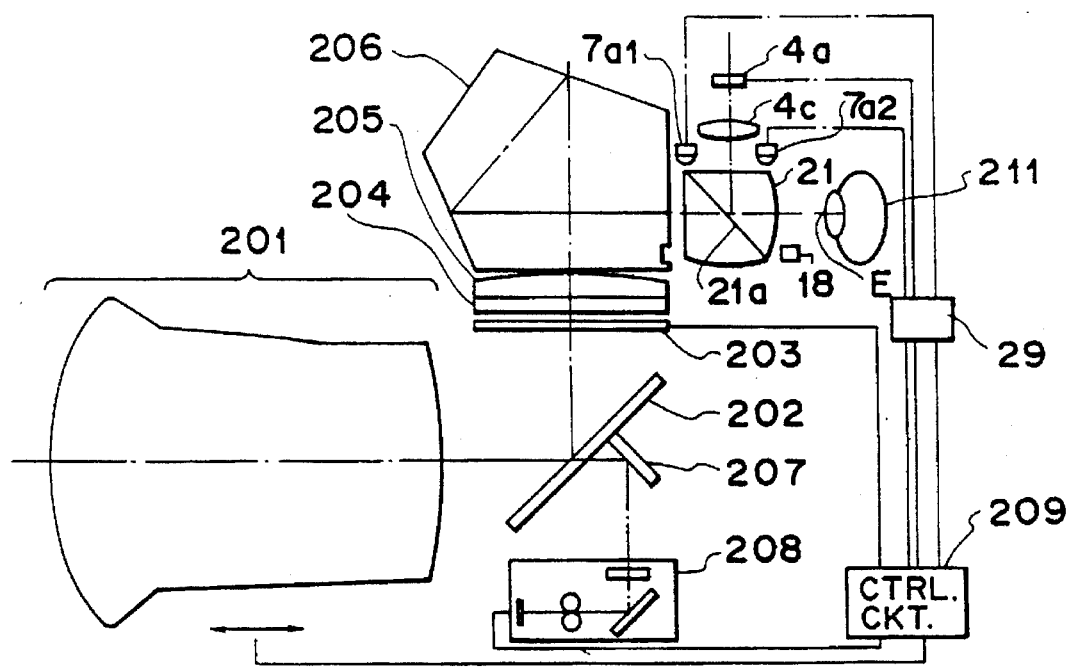
FIGS. 2A and 2B are schematic views showing, a main part when the present invention is applied to a single-lens reflex camera.
Figure 2B:
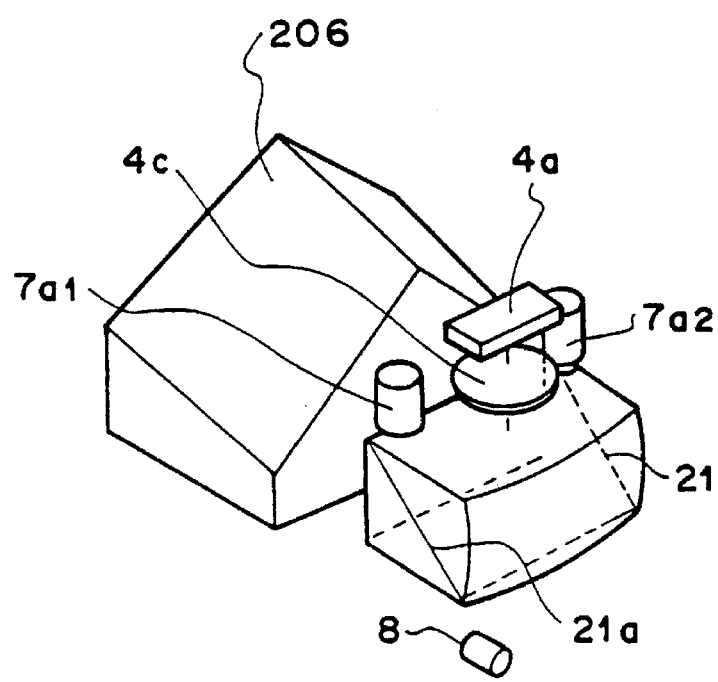

FIG. 1 is a block diagram showing a main part of the first embodiment when a pupil center detection method of the present invention is applied to a single-lens reflex camera. FIG. 2A is a schematic view showing a main part when the pupil center detection method of the present invention is applied to a single-lens reflex camera for a silver chloride film or still video, and FIG. 2B is a partial perspective view showing a main part of FIG. 2A.

Figure 18:
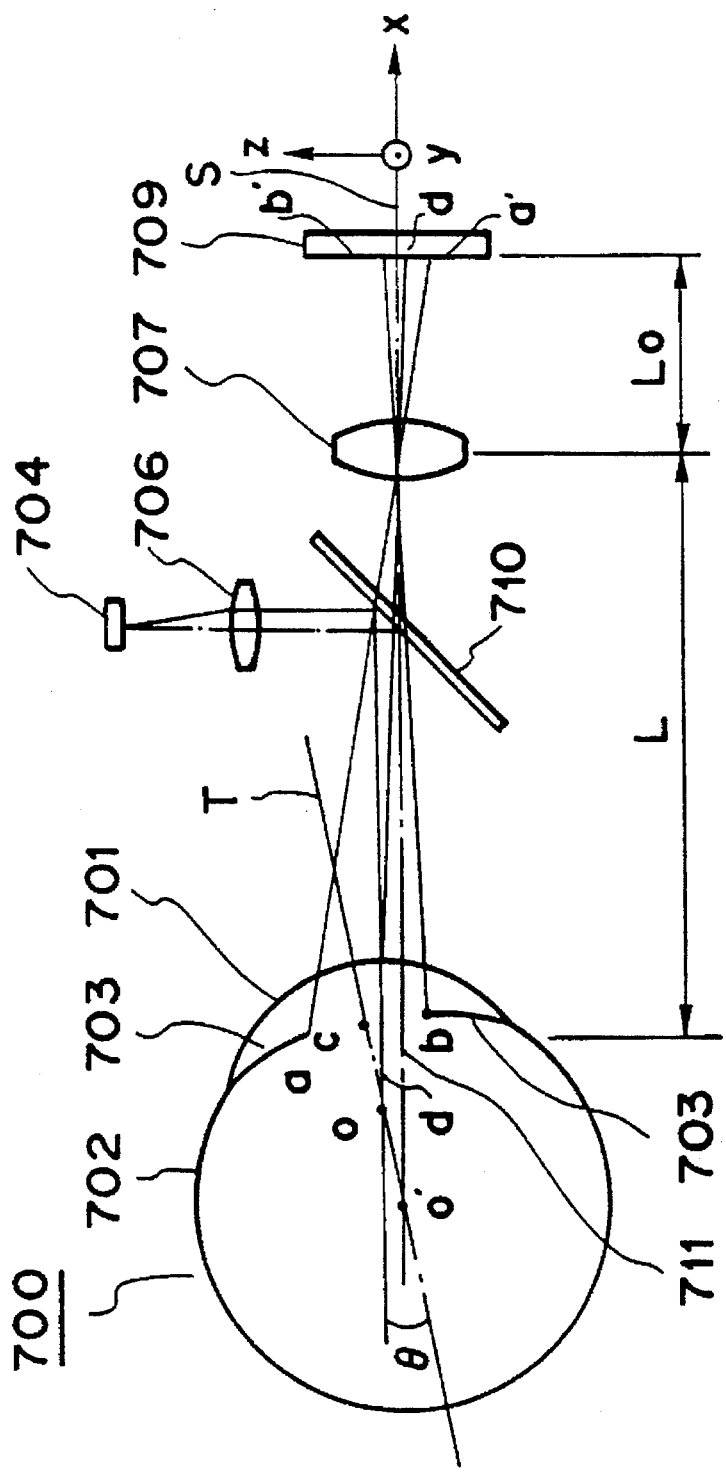
FIG. 18 is a schematic view showing a main part of a conventional sight axis detection apparatus.
Figure 19A:
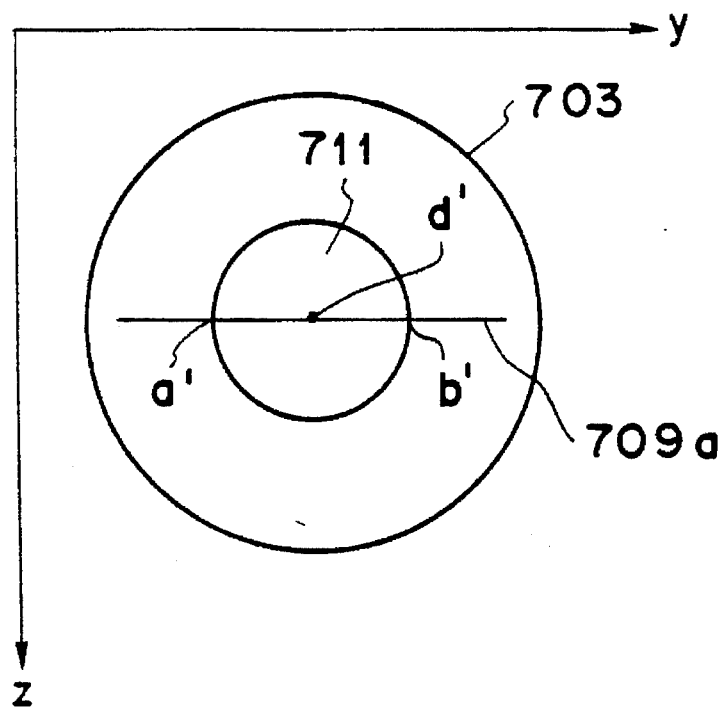
FIGS. 19A and 19B are partial explanatory views of FIG. 18.
Figure 19B:
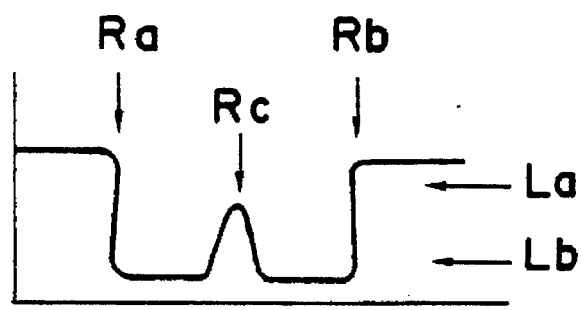
Figure 20:
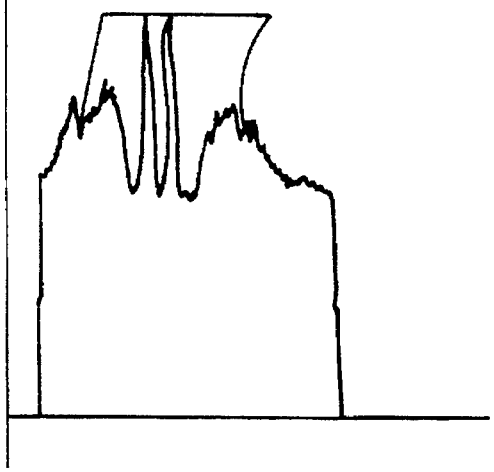
FIG. 20 is a waveform chart of a signal obtained from a sensor shown in FIG. 18.
Figure 21:
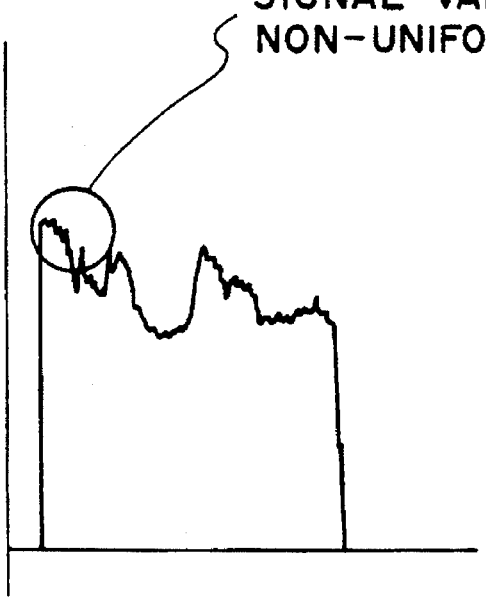
FIG. 21 is a waveform chart of another signal obtained from the sensor shown in FIG. 18.
Figure 22:
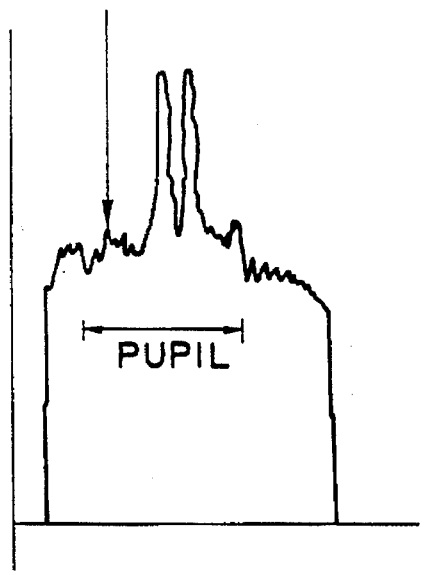
FIG. 22 is a waveform chart of still another signal obtained from the sensor shown in FIG. 18.
Figure 23:
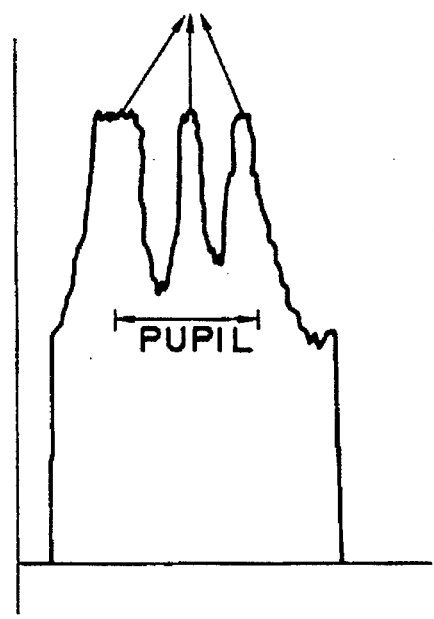
FIG. 23 is a waveform chart of still another signal obtained from the sensor shown in FIG. 18.

In this embodiment, a detection apparatus of specific points based on light beams reflected by an eyeball can be explained by referring to a conventional optical system shown in FIG. 18.

In FIG. 1, a microprocessing unit (M.P.U.) 1 performs various calculation processing operations such as a sight axis calculation using position information of a first Purkinje image and a pupil. A memory 2 stores, e.g., signals associated with the integration time of an image sensor (to be described later). An interface circuit 3 has an A/D conversion function. A projection means 7 causes infrared light-emitting diodes 7a to radiate infrared light unsensible by an observer onto the eyeball of the observer via a projection lens 7b.

A light emission control circuit (light emission control means) 5 controls the light emission amount of the infrared light-emitting diodes 7a. A position sensor 6 detects the vertical and horizontal postures of a camera to which the sight axis detection apparatus is applied. A detection means 4 comprises an image sensor 4a, a driving circuit 4b, a light-receiving lens 4c, and the like, and forms a first Purkinje image and an image of a pupil based on light reflected by the eyeball on the surface of the image sensor 4a via the light-receiving lens 4c. The apparatus also includes an AF sensor 8, a lens driver unit 9, a photometry sensor 10, and an aperture driver unit 11.

The arrangement adopted when the present invention is applied to a single-lens reflex camera will be described below with reference to FIGS. 2A and 2B.

An optical system shown in FIG. 2A includes an eyepiece lens 21 in which a dichroic mirror 21a for transmitting visible light therethrough and reflecting infrared light is obliquely arranged, and which serves as an optical path splitter, the image sensor 4a, the light-receiving lens 4c, and light sources. 7a1 and 7a2 constituting the projection means 7, and comprising, e.g., light-emitting diodes.

The image sensor 4a is constituted by two-dimensional arrays of photoelectric elements, and is arranged at a position conjugate with a position near the pupil of an eye located at a predetermined position (a general eye-point position of a photographer who does not wear eyeglasses) with respect to the light-receiving lens 4c and the eyepiece lens 21. The photometry sensor 8 is arranged near the eyepiece lens 21.

A processor 29 has a sight axis correction calculation function, a sight axis correction data storage function, and a sight axis calculation function, and comprises the M.P.U. 1, the light emission control circuit 5, the memory 2, the interface circuit 3, and the like shown in FIG. 1.

The optical system also includes a photographing lens 201, a quick return (QR) mirror 202, a display element 203, a focusing screen 204, a condenser lens 205, a pentagonal prism 206, a sub mirror 207, and a multi-point focus detection unit 208 for executing focus detection by selecting a plurality of areas in a photographing frame by a known method. A camera control circuit 209 has an intra-finder display element driving function, a focus detection calculation function, a lens driving function, and the like.

In this embodiment, some light components of object light transmitted through the photographing lens 201 are reflected by the QR mirror 202, and form an object image near the focusing screen 204. The object light diffused by the diffusion surface of the focusing screen 204 is guided to an eye point E via the condenser lens 205, the pentagonal prism 206, and the eyepiece lens 21.

The display element 203 comprises, e.g., a two-layered Guest-Host type liquid crystal element using no polarization plate, and displays distance measuring areas (focus detection positions) in the finder field.

Some other light components transmitted through the photographing lens 201 are transmitted through the QR mirror 202, are reflected by the sub-mirror 207, and are guided to the above-mentioned multi-point focus detection unit 208 arranged on the bottom portion of the camera main body. Furthermore, a photographing lens driver unit (not shown) extends (or retracts) the photographing lens 201 on the basis of focus detection information at a position on the object surface selected by the multi-point focus detection unit 208, thus performing focus adjustment.

In this embodiment, infrared light beams emitted from the infrared light-emitting diodes 7a1 and 7a2 are incident on the eyepiece lens 21 from above in FIG. 2A, are reflected by the dichroic mirror 21a, and divergently illuminate an eyeball 211 of the observer located near the eye point E. The infrared light reflected by the eyeball 211 is reflected by the dichroic mirror 21a, and forms an image on the image sensor 4a while being converged by the light-receiving lens 4c.

In this embodiment, sight axis detection is performed based on two amounts, i.e., a first Purkinje image (cornea reflecting image) and a pupil center calculated based on a plurality of pupil ring portions, which are obtained by executing calculation processing of output signals from the image sensor 4a. The sight axis detection utilizes the fact that when the eyeball 211 of the photographer is illuminated with light emitted from the infrared light-emitting diodes 7a from the front side, the generation position of a virtual image of the infrared light-emitting diode, i.e., a so-called Purkinje image coincides with the position of the pupil center when the rotational angle of the eyeball (i.e., the optical axis of the eyeball) is zero, and the generation position deviates as the eyeball rotates.

Since the deviation (interval) between the Purkinje image and the pupil center is almost proportional to the sine of the rotational angle, the interval is calculated from the positions of the Purkinje image and the pupil center, and the rotational angle of the eyeball is then subjected to, e.g., a sight axis correction calculation, thus obtaining the sight axis of the photographer.

The operation of the present invention using the above-mentioned method will be described below.

Figure 3:
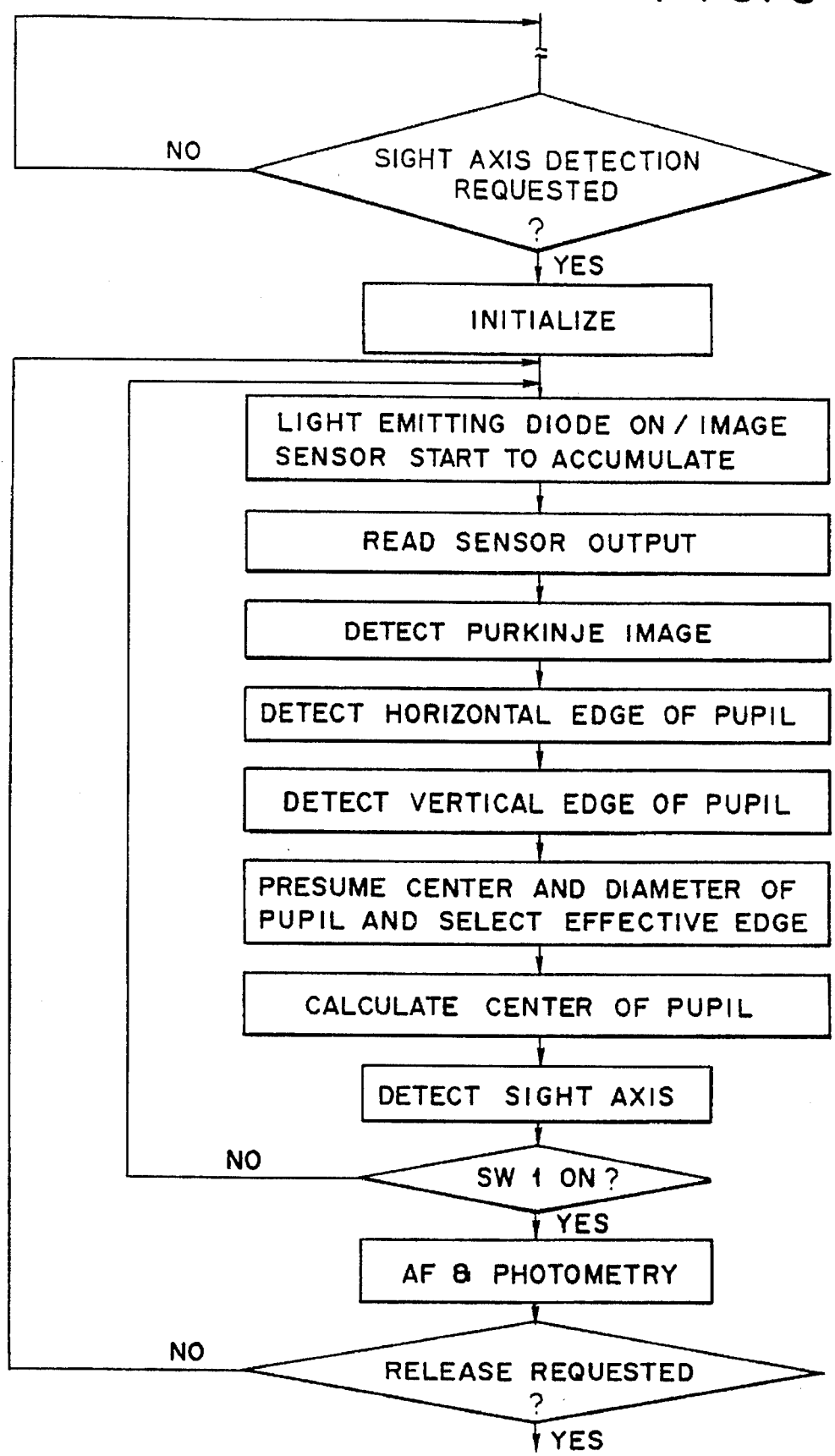
FIG. 3 is a flow chart showing a sight axis detection routine.

When a main switch (not shown) of the camera is turned on to request the start of sight axis detection, the control of the M.P.U. 1 enters a sight axis detection routine. FIG. 3 is a flow chart showing the sight axis detection routine. When the control newly enters the sight axis detection routine, initialization processing is performed to initialize all variables associated with sight axis detection. Upon reception of information of the posture position (vertical or horizontal position) of the camera at that time from the position sensor 6, the light emission control circuit 5 selects infrared light-emitting diodes (iRED) 7a to be driven. At the same time, the M.P.U. 1 supplies, via the interface circuit 3, an integration signal to the driving circuit 4b and a light emission control signal synchronous with the integration signal to the light emission control circuit 5. With these signals, the infrared light-emitting diodes 7a, which correspond to the posture of the camera at that time, emit light in synchronism with the accumulation operation of the image sensor 4a.

An image of the front eye part of the eyeball corresponding to a Purkinje image formed on the image sensor 4a is read through the interface circuit 3. By processing the read image, a position P of the Purkinje image, a plurality of pupil ring portions (so-called pupil edges) $D_i$, and a pupil center Dc ($x_0$, $y_0$) are detected. At this time, the average value and standard deviation of the pupil ring portions $D_i$ are calculated, and the pupil center Dc is calculated using data within a range defined by the above-mentioned two values. Then, horizontal and vertical rotational angles $\theta_H$ and $\theta_V$ of the eyeball are calculated from the detected values. After the rotational angles of the eyeball are calculated, a personal difference correction such as a sight axis correction is performed to obtain a view point, on the focusing screen, of the photographer.

The above-mentioned operations are repeated until a release button of the camera is depressed to its half-stroke position to turn on a switch SW1. When the switch SW1 is turned on, the view point information, on the focusing screen, of the photographer obtained, as described above, is fed back to various operations such as an AF operation, a photometry operation, and the like of the camera. For example, in the AF operation, the M.P.U. 1 performs an AF calculation using a signal of a portion, corresponding to the view point, of the AF sensor 8 to obtain a lens driving amount for achieving an in-focus state. Thereafter, the M.P.U. 1 performs focus adjustment by controlling the lens driver unit 9.

Also, in the photometry operation, the M.P.U. 1 calculates exposure constants (a shutter speed, an aperture value, and the like) according to a designated photographing mode on the basis of a signal of a portion, corresponding to the view point, of the photometry sensor 10. When a release request is issued, the M.P.U. executes a series of release operations such as an operation for driving the aperture to the calculated aperture value, an operation for opening/closing a shutter, a film wind-up operation, and the like.

Note that the view point of the photographer does not always coincide with an object, but may often fluctuate or may move to an indication outside the frame. Thus, it is preferable to execute processing for omitting the view point outside the frame, processing for extracting the view point of the photographer by a method proposed in, e.g., Japanese Laid-Open Patent Application No. 3-109030, and the like.

Figure 4:
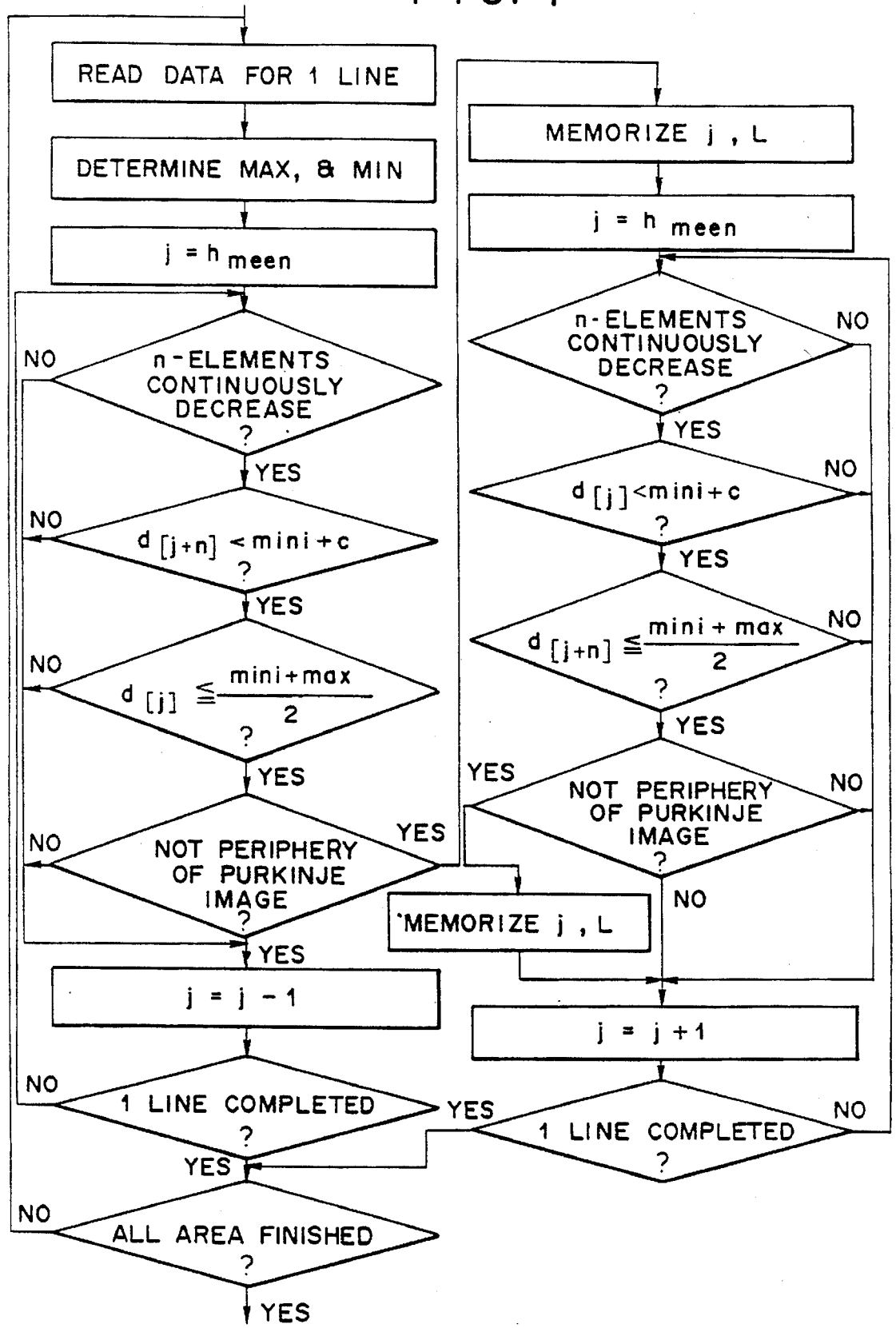
FIG. 4 is a flow chart showing the first embodiment of a pupil central position detection routine.

The routine for obtaining the pupil ring portion (pupil edge) positions $D_i$ will be described in detail below. FIG. 4 is a flow chart showing this routine.

As described above, when the control enters the sight axis detection routine, the memory content is initialized, the infrared light-emitting diodes (iRED) are caused to emit light, signal outputs from the sensor are read, and so on. Based on the read output signals, Purkinje images are detected, and the detection result is stored in the memory. Since the number of Purkinje images to be generated coincides with the number of IREDs which emit light, a plurality of Purkinje images are generated in the case of the present invention using a plurality of iREDs. When the coordinates of these images on the sensor are represented by $(h_1, v_1)$, $(h_2, v_2)$, ..., $(h_n, v_n)$, the vertical coordinates $v_1, v_2, ..., v_n$ substantially coincide with each other in the arrangement of the optical system of the present invention. Therefore, the start point of a horizontal pupil edge extraction calculation is defined by a mean value $h_{mean}$ of the horizontal coordinates $h_1, h_2, ..., h_n$ of the plurality of Purkinje images. The mean value $h_{mean}$ is given by:

$$h_{mean} = \sum_{i=1}^{n} h_i/n$$

On the other hand, the vertical start point is obtained by subtracting an optically determined constant $v_{const}$ from one of $v_1, v_2, ..., v_n$, e.g., $v_1 - v_{const}$. In this manner, a point $(h_{mean}, v_1 - v_{const})$ becomes a point inside the pupil with a very high probability.

Thus, when the horizontal and vertical pupil edge extraction operations are respectively started from $h_{mean}$ and $v_1 - v_{const}$, the calculations can be started from minimum luminance portions of the entire image (all signals), and it is suitable for extracting pupil edges as leading edges from the minimum luminance portions.

Thereafter, when the control enters the horizontal pupil edge detection routine, data for one line is read, and the positions of pupil edges for this line are detected. A maximum value (max) and a minimum value (mini) are obtained from the read 1-line data. These two values are the maximum and minimum values of the line read at that time, and do not always coincide with maximum and minimum values of the entire image.

The M.P.U. starts a detection calculation from an $(h_{mean})$-th (when $h_{mean}$ is not a natural number, a natural number closest to $h_{mean}$) pixel. First, a left pupil edge is detected by decrementing a counter. The M.P.U. checks if the output signal continuously decreases over n pixels, i.e., checks if the following relation is satisfied:

$$d_{[j]} < d_{[q-1]} < d_{[j-2]} < \ldots < d_{[j-(n-1)]} < d_{[j-n]}$$

Then, the M.P.U. checks if $d_{[j+n]}$ corresponding to the minimum value of the slope is substantially equal to the minimum value (mini) of the read line, i.e., if $d_{[j+n]} \leq \text{mini} + c$ is satisfied. Furthermore, the M.P.U. checks if $d_{[j]}$ corresponding to the maximum value of the slope is smaller than an average value (mini+max)/2 of the maximum and minimum values of the read line. Thus, a falling slope from the iris portion where the signal intensity is equal to or smaller than the average value of the maximum value (max) and the minimum value (mini) to the pupil where the signal intensity is substantially equal to the minimum value can be detected.

Furthermore, whether or not this point is present near the periphery of the previously obtained Purkinje image is checked to prevent a detection error due to the influence of the Purkinje image (a signal inside the pupil may often have an upward projecting waveform due to the influence of the Purkinje image near the periphery of the Purkinje image, and the upward projecting waveform may often be erroneously detected as a pupil edge).

A position satisfying the above-mentioned four conditions is determined as a pupil edge, and a line number L and a pixel number j of the position are stored in the memory as pupil edge information. Thereafter, the M.P.U. enters a routine for detecting an opposite (right) pupil edge. Conversely, when the above-mentioned conditions are not satisfied, the same processing is performed for a neighboring pixel. In the routine for detecting the opposite pupil edge, the same processing is performed.

More specifically, it is checked if a position satisfies the following four conditions:

(1-1) the output signal continuously increases over n pixels;

(1-2) $d_{[j]}$ corresponding to the minimum value of a slope is substantially equal to the minimum value (mini);

(1-3) $d_{[j+n]}$ corresponding to the maximum value of the slope is equal to or smaller than an average value of the maximum value (max) and the minimum value (mini); and (1-4) the corresponding point is not present near the periphery of the previously obtained Purkinje image.

If the position satisfies these conditions, it is determined to be a pupil edge, and a line number L and a pixel number j of the position are stored in the memory as pupil edge information, thus ending processing for one line.

Conversely, if the conditions are not satisfied, the processing is performed for a neighboring pixel. With this processing, the memory can store position information of the innermost right and left pupil edges (see FIG. 5).

The above-mentioned processing is performed over the entire frame in units of lines to obtain a plurality of pupil edge positions. Upon completion of the processing for the entire frame, the control enters a vertical pupil edge detection routine. In this routine, the same processing as described above is performed to have $v_1 - v_{const}$ as the start point of the pupil edge extraction calculation to obtain pupil edges. In this routine, however, since the maximum and minimum values of signals on the entire frame have already been determined in the horizontal pupil edge detection routine, these values are used in the calculation of this routine, and a calculation for obtaining the maximum and minimum values is omitted.

Figure 6:
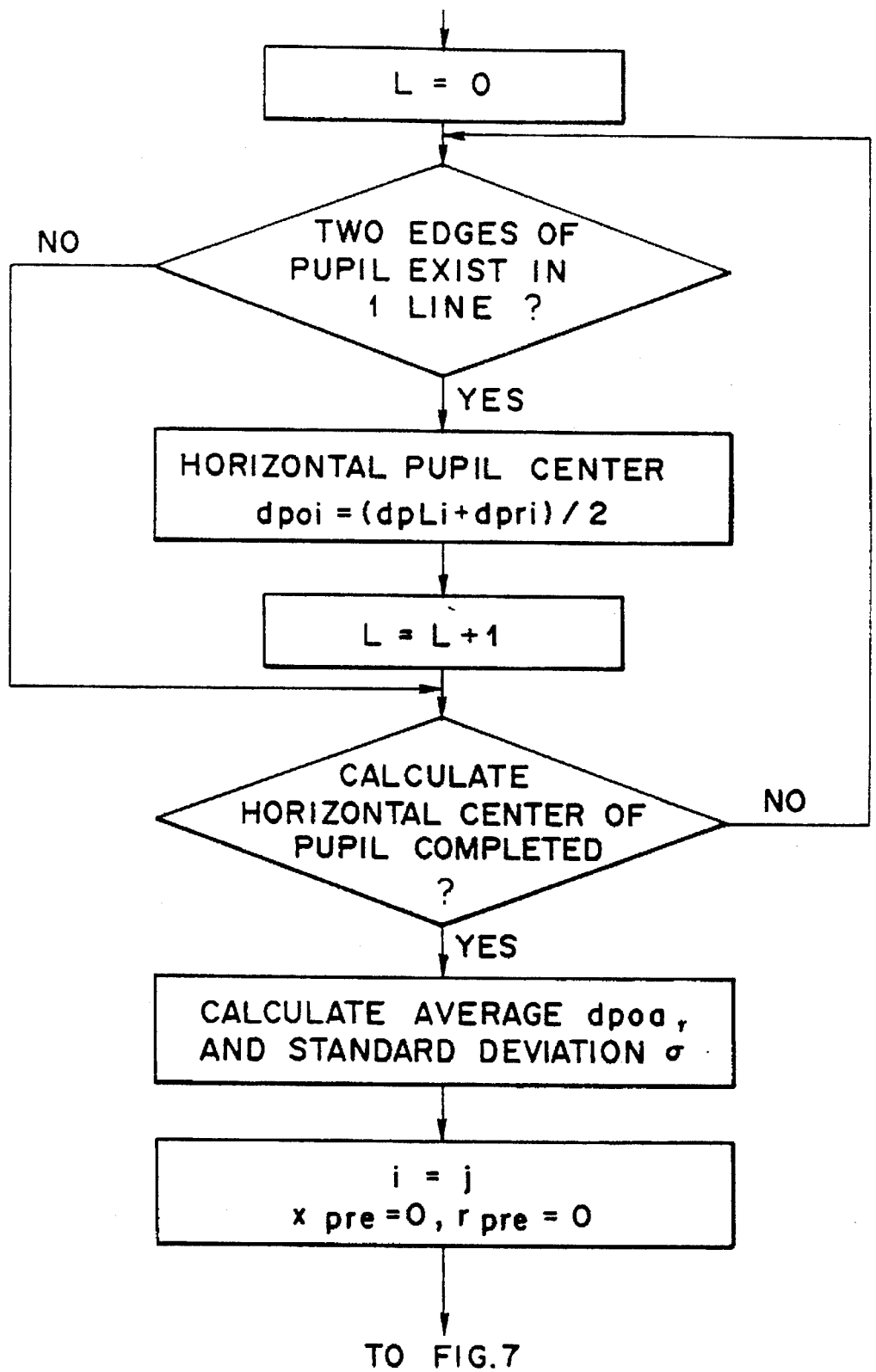
FIG. 6 is a flow chart showing a pupil center detection routine.
Figure 7:
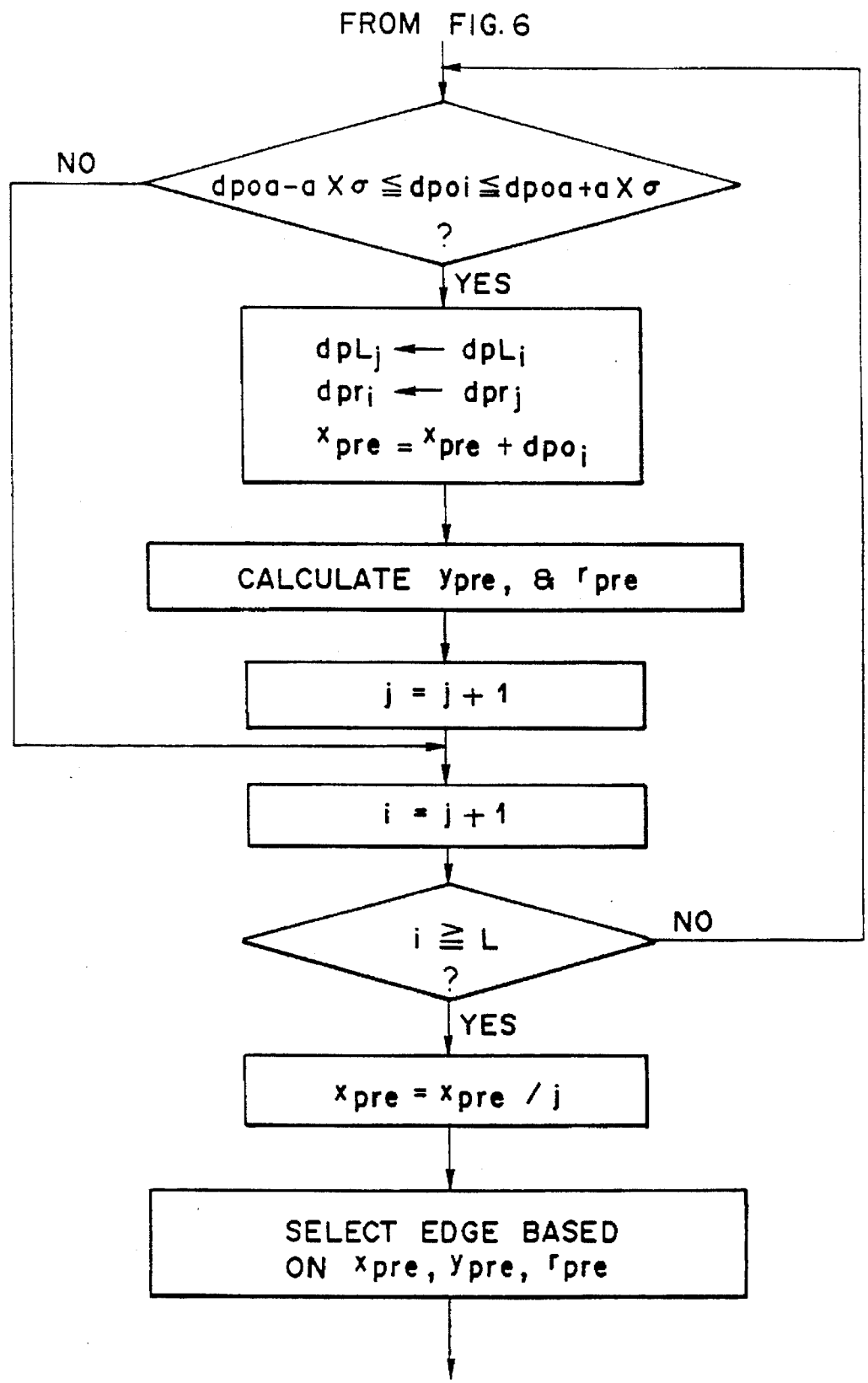
FIG. 7 is a flow chart showing the pupil center detection routine.

Upon completion of the horizontal and vertical pupil edge extraction operations, the pupil center Dc $(x_0, y_0)$ is finally calculated from these pieces of information. In this case, the pupil may be assumed to be a circle, and a method of least squares may be used. In addition, an operation for selecting data used upon calculation of the pupil center Dc $(x_0, y_0)$ is performed. This operation is performed as follows. FIGS. 6 and 7 show the operation sequence.

The M.P.U. obtains horizontal pupil central positions $dpo_i$ in units of lines using information of the horizontal pupil edge positions obtained in the above operations, and at the same time, counts the number L of the obtained positions $dpo_i$. Information corresponding to only one pupil edge on a single line is determined to be a detection error, and is not used in a future calculation.

An average value dpoa and a standard deviation σ are calculated using the horizontal pupil central positions $dpoa_i$ according to the following equations:

$$dpoa = \frac{\sum_{i=1}^{L} dp_i}{L}$$

$$\sigma^2 = \frac{\sum_{i=1}^{L} (dp_i^2)}{L} - (dpoa)^2$$

Using these two calculated values, the effective range of the horizontal pupil center $dpo_i$ is determined as $dpoa - a \times \sigma \leq dpo_i \leq dpo + a \times \sigma$ (where a is an arbitrary constant determined by an image signal state such as a contrast of an image). When the range is determined, it is checked if each $dpo_i$ falls within this range. If a given position $dpo_i$ falls within this range, two horizontal pupil edge positions $dpL_i$ and $dpr_i$ used upon calculation of the given position $dpo_i$ are stored as $dpL_j$ and $dpr_j$. Then, this $dpo_i$ is added to a counter for obtaining a presumed horizontal pupil center $x_{pre}$. A presumed vertical pupil center $y_{pre}$ and a presumed pupil diameter $r_{pre}$ are calculated as follows.

First, the absolute value of a difference between $dpL_i$ and $dpr_i$ is calculated, and is compared with a presumed pupil diameter $r_{pre}$ (an initial value of $r_{pre}$ is zero) detected so far. If $abs(dpL_i - dpr_i) > r_{pre}$ is satisfied, $abs(dpL_i - dpr_i)$ is adopted as new $r_{pre}$. At the same time, the vertical coordinate at that time is stored as a presumed vertical pupil center $y_{pre}$. This operation is repeated a plurality of number of times corresponding to the number L of obtained $dpo_i$.

After the control exits the above-mentioned loop, the content of the counter for obtaining $x_{pre}$ is divided by the number j of $dpo_i$ present within the range of $dpoa - a \times \sigma \leq dpo_i \leq dpo + a \times \sigma$, thus obtaining the presumed horizontal pupil center $x_{pre}$.

Figure 8:
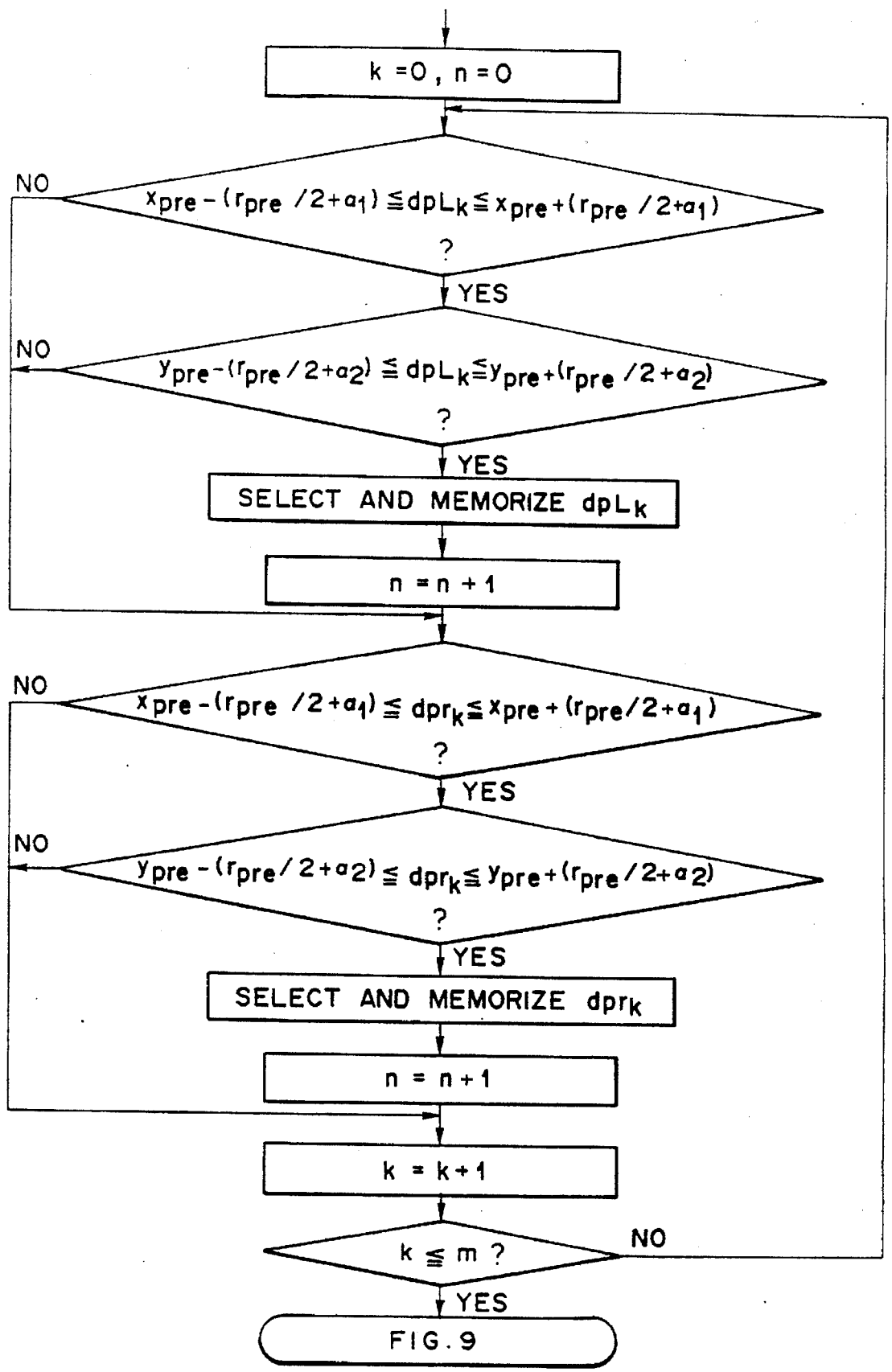
FIG. 8 is a flow chart showing a pupil edge selection routine using a presumed pupil central position and a presumed pupil diameter.
Figure 9:
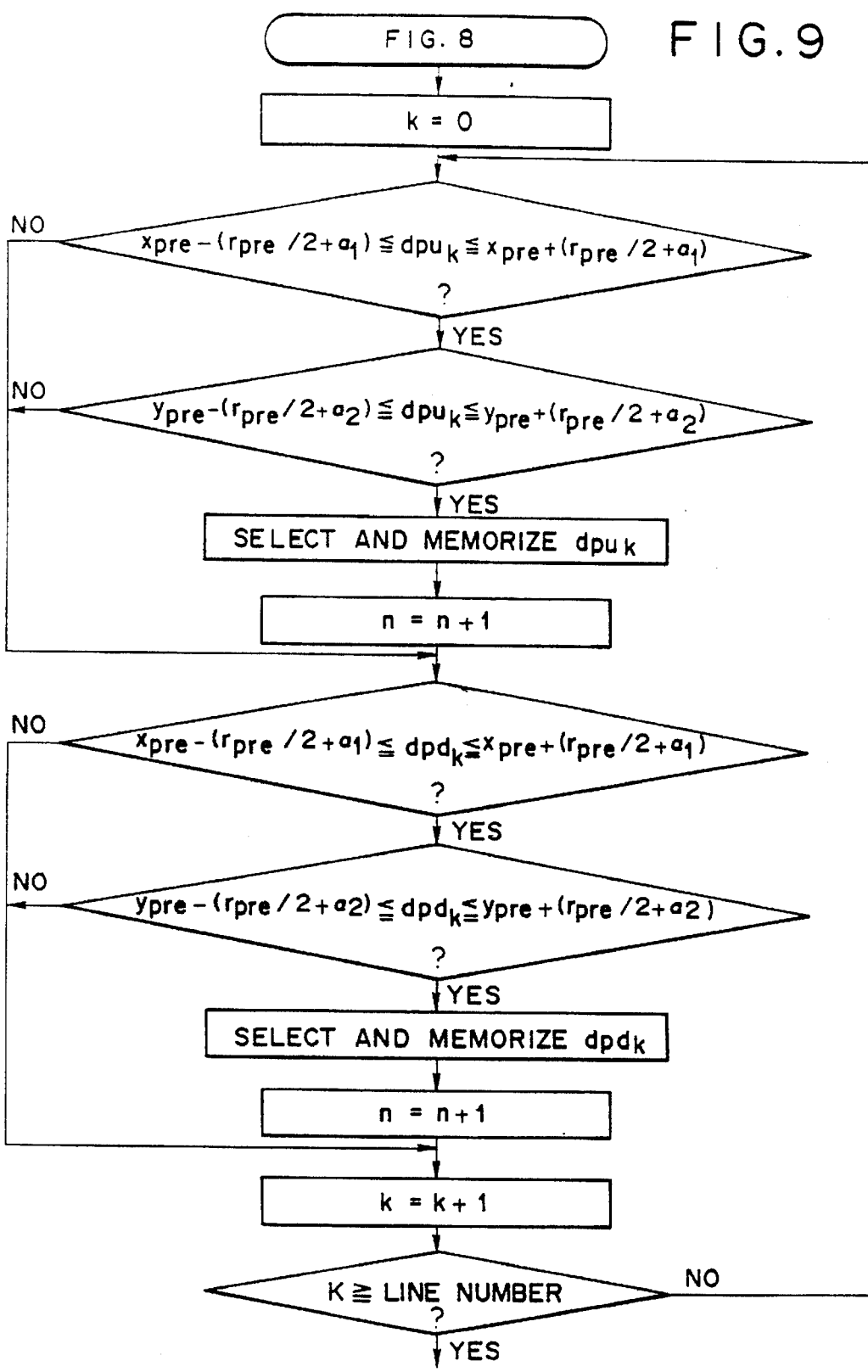
FIG. 9 is a flow chart showing the pupil edge selection routine using the presumed pupil central position and the presumed pupil diameter.

Then, an edge selection operation is performed using the calculated presumed pupil central positions $x_{pre}$ and $y_{pre}$ and the presumed pupil diameter $r_{pre}$ (see FIGS. 8 and 9). The M.P.U. selects information falling within ranges of $x_{pre} \pm (r_{pre}/2 + \alpha_1)$ and $y_{pre} \pm (r_{pre}/2 + \alpha_2)$. That is, the M.P.U. determines and selects, as effective pupil edge information, information present within a rectangle which is defined by sides $r_{pre} + 2\alpha_1$ and $r_{pre} + 2\alpha_2$ to have $(x_{pre}, y_{pre})$ as the center.

More specifically, it is checked if right, left, upper, and lower pupil edge positions fall within a range of a rectangle surrounded by four points given by:

$$(x_{pre}-(r_{pre}/2+\alpha_1), y_{pre}-(r_{pre}/2+\alpha_2))$$

$$(x_{pre}-(r_{pre}/2+\alpha_1), y_{pre}+(r_{pre}/2+\alpha_2))$$

$$(x_{pre}+(r_{pre}/2+\alpha_1), y_{pre}-(r_{pre}/2+\alpha_2))$$

$$(x_{pre}+(r_{pre}/2+\alpha_1), y_{pre}+(r_{pre}/2+\alpha_2))$$

Information falling within the range is determined and selected as effective information. In this case, $\alpha_1$ and $\alpha_2$ are constants determined in consideration of a presumption error of $r_{pre}$, and are determined depending on the state of an image signal like in the above-mentioned constant $\underline{a}$.

When extraction and selection of the horizontal and vertical pupil edges are ended, as described above, a pupil center Dc ($X_0$, $Y_0$) is calculated using the selected information. As an effective calculation method, a pupil may be assumed to be a circle, and a method of least squares may be used.

The second embodiment of a pupil center detection method according to the present invention will be described hereinafter. In the second embodiment, in order to select effective information from extracted pupil edge information with still higher precision, an average value and a standard deviation are calculated a plurality of number of times. More specifically, an average value $dpoa_{second}$ and a standard deviation $\sigma_{second}$ are calculated using positions $dpo_i$ falling within a range ($dpoa_{first} - a \times \sigma_{first} \leq dpo_i \leq dpoa_{first} + a \times \sigma_{first}$) defined by an average value $dpoa_{first}$ and a standard deviation $\sigma_{first}$ calculated in the first calculation. Then, positions $dpo_i$ falling within a range ($dpoa_{second} - a \times \sigma_{second} \leq dpo_i \leq dopa_{second} + a \times \sigma_{second}$) defined by the average value $dpoa_{second}$ and the standard deviation $\sigma_{second}$ are determined to be effective information, and are used in a calculation of the pupil center Dc ($X_0$, $Y_0$).

The arrangement and the operation sequence of the second embodiment are respectively shown in FIGS. 1 and 3. As in the first embodiment, when the start of sight axis detection is requested, and the control newly enters the sight axis detection routine, initialization processing is performed to initialize all variables associated with sight axis detection. Upon reception of information of the posture position (vertical or horizontal position) of the camera at that time from the position sensor 6, the light emission control circuit 5 selects infrared light-emitting diodes (iRED) 7a to be driven.

At the same time, the M.P.U. 1 supplies, via the interface circuit 3, an integration signal to the driving circuit 4b and a light emission control signal synchronous with the integration signal to the light emission control circuit 5. With these signals, the accumulation operation of the image sensor 4a, and the light emission operation of the iREDs corresponding to the camera posture are synchronously performed.

An image of the front eye part of the eyeball corresponding to a Purkinje image formed on the image sensor 4a is read through the interface circuit 3. By processing the read image, a position P of the Purkinje image and a plurality of pupil ring portions (so-called pupil edges) $D_i$ are detected.

The average value and the standard deviation of these edges $D_i$ are calculated, and edges falling within a range defined by these two values are determined as effective edges. The average value and the standard deviation of the effective edges are calculated again, and a pupil center Dc ($X_0$, $Y_0$) is calculated using only edges falling within a range defined by these two values. Horizontal and vertical rotational angles $\theta_H$ and $\theta_V$ of the eyeball are calculated using the detected values. Furthermore, a personal difference correction such as a sight axis correction is performed to obtain a view point, on the focusing screen, of the photographer.

The above-mentioned operations are repeated until a release button of the camera is depressed to its half-stroke position to turn on a switch SW1. When the switch SW1 is turned on, the view point information, on the focusing screen, of the photographer obtained, as described above, is fed back to various operations such as an AF operation, a photometry operation, and the like of the camera. When a release request is issued, the M.P.U. executes a series of release operations such as an operation for driving an aperture to a calculated aperture value, an operation for opening/closing a shutter, a film wind-up operation, and the like.

Figure 10:
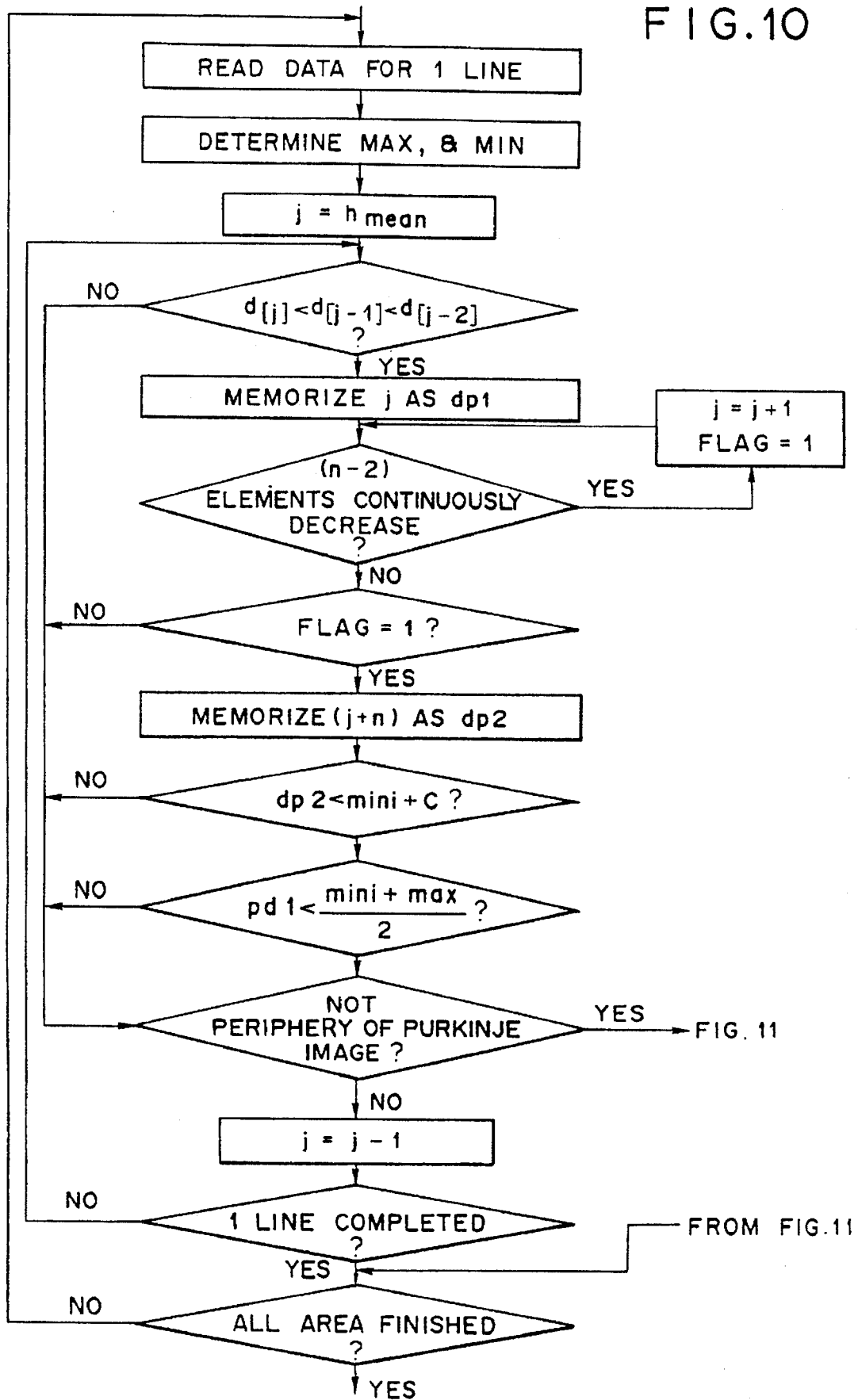
FIG. 10 is a flow chart showing the second embodiment of a pupil central position detection routine.
Figure 11:
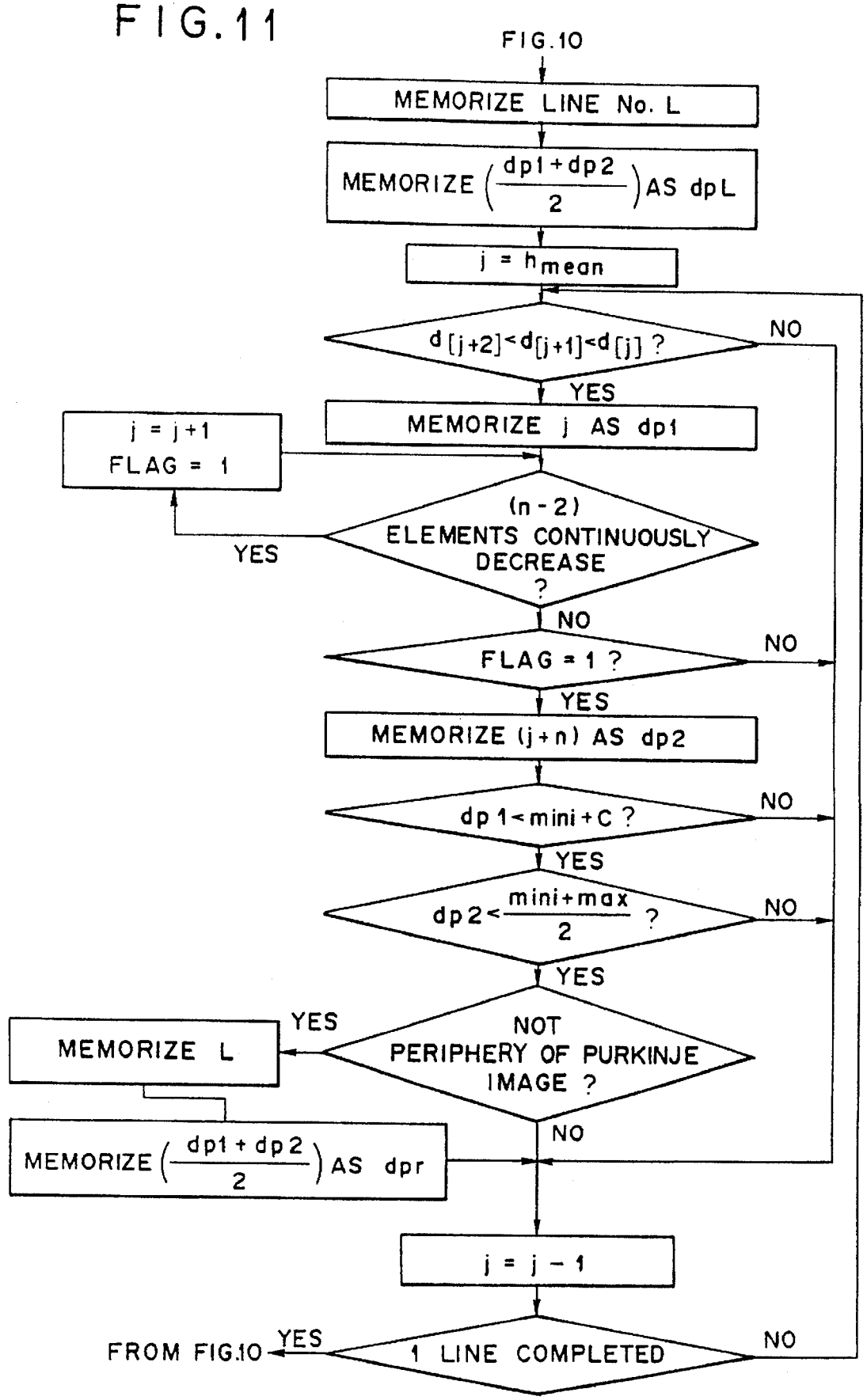
FIG. 11 is a flow chart showing the second embodiment of the pupil central position detection routine.

A routine for calculating pupil edge positions $D_i$ will be described in detail below. FIGS. 10 and 11 are flow charts showing this routine.

As described above, when the control enters the sight axis detection routine, the memory content is initialized, the infrared light-emitting diodes (iRED) are caused to emit light, signal outputs from the sensor are read, and so on. Based on the read output signals, Purkinje images are detected, and the detection result is stored in the memory. Since the number of Purkinje images to be generated coincides with the number of IREDs which emit light, a plurality of Purkinje images are generated in the case of this embodiment using a plurality of iREDs. When the coordinates of these images on the sensor are represented by ($h_1$, $v_1$), ($h_2$, $v_2$), . . . , ($h_n$, $v_n$), the vertical coordinates $v_1$, $v_2$, . . . , $v_n$ substantially coincide with each other in the arrangement of the optical system.

Therefore, the start point of a horizontal pupil edge extraction calculation is defined by a mean value $h_{mean}$ of the horizontal coordinates $h_1$, $h_2$, . . . , $h_n$ of the plurality of Purkinje images. The mean value $h_{mean}$ is given by:

$$h_{mean} = \sum_{i=1}^{n} h_i / n$$

On the other hand, the vertical start point is obtained by subtracting an optically determined constant $v_{const}$ from one of $v_1$, $v_2$, . . . , $v_n$, e.g., $v_1 - v_{const}$.

In this manner, a point ($h_{mean}$, $v_1 - v_{const}$) is located inside the pupil with a very high probability. Thus, when the horizontal and vertical pupil edge extraction operations are respectively started from $h_{mean}$ and $v_1 - v_{const}$, the calculations can be started from minimum luminance portions of the entire image (all signals), and it is suitable for extracting pupil edges as leading edges from the minimum luminance portions.

Thereafter, when the control enters the horizontal pupil edge detection routine, data for one line is read, and the positions of pupil edges for this line are detected. A maximum value (max) and a minimum value (mini) are obtained from the read 1-line data. These two values are the maximum and minimum values of the line read at that time, and do not always coincide with maximum and minimum values of the entire image.

The M.P.U. starts a detection calculation from an ($h_{mean}$)-th pixel. First, a left pupil edge is detected by decrementing a counter.

The M.P.U. checks if the output signal continuously decreases over n pixels. More specifically, as shown in FIGS. 10 and 11, the M.P.U. obtains a point which satisfies the following relation, i.e., the start point of the decrease, and stores the point in the memory as dp1:

$$d_{[j]} < d_{[j-1]} < d_{[j-2]}$$

Then, the M.P.U. searches points satisfying the following relation, i.e., points where the output signal continuously decreases over (n–2) pixels:

$$d_{[j-2]} < d_{[j-3]} < \ldots < d_{[j-n]}$$

Since (n–2) pixels are set, a position where the output signal continuously decreases over n pixels is obtained in combination with the above condition.

As in the first embodiment, j is incremented while the conditions are satisfied; when the conditions are not satisfied, the control exits the loop, and the position at that time is stored as dp2 in the memory. However, as in the first embodiment, when the control exits the loop without satisfying the conditions any time, no data is stored in the memory, and the processing is performed for a neighboring pixel.

It is then checked if dp2 corresponding to the minimum value of a slope is substantially equal to the minimum value (mini) of the read line, and it is also checked if dp1 corresponding to the maximum value of the slope is smaller than an average value (mini+max)/2 of the maximum and minimum values of the read line. Thus, a falling slope from the iris where the signal intensity is equal to or smaller than the average value of the maximum value and the minimum value to the pupil where the signal intensity is substantially equal to the minimum value can be detected. Furthermore, whether or not dp1 and dp2 are present near the periphery of the previously obtained Purkinje image is checked to prevent a detection error caused by the influence of the Purkinje image.

A position satisfying the above-mentioned four conditions is determined to be a pupil edge, and an average value of dp1 and dp2 is stored as left pupil edge information (dpL) together with its line number L. When a position satisfying the four conditions is found, the information of the position is stored in the memory, and thereafter, the control enters a routine for detecting an opposite (right) pupil edge; otherwise, the same processing is performed for a neighboring pixel.

In the routine for detecting the opposite pupil edge, the same processing is performed. More specifically, when a certain position satisfies the following four conditions, the position is determined to be a pupil edge, dpr (=(dp1+dp2)/2) and a line number L are stored in the memory as the information of the position, and thereafter, the processing is performed for a neighboring pixel.

(2-1) A point satisfying $d_{[j]} < d_{[j+1]} < d_{[j+2]}$ corresponding to the start point of an increase and a point satisfying $d_{[j+2]} < d_{[j+3]} < \ldots < d_{[j+n]}$ corresponding to the end point of the increase are present.

(2-2) dp1 (=$d_{[j]}$) corresponding to the minimum value of a slope is substantially equal to the minimum value (mini).

(2-3) dp2 (=$d_{[j+n]}$) corresponding to the maximum value of the slope is equal to or smaller than an average value of the maximum value (max) and the minimum value (mini).

(2-4) The corresponding point is not present near the periphery of the previously obtained Purkinje image.

The above-mentioned processing is performed over the entire frame in units of lines to obtain a plurality of pupil edge positions.

Upon completion of the processing for the entire frame, the control enters a vertical pupil edge detection routine. In this routine, the same processing as described above is performed to have $v_1 – v_{const}$ as the start point of the pupil edge extraction calculation to obtain pupil edges. In this routine, however, since the maximum and minimum values of signals on the entire frame have already been determined in the horizontal pupil edge detection routine, these values are used in the calculation of this routine, and a calculation for obtaining the maximum and minimum values is omitted.

Figure 12:
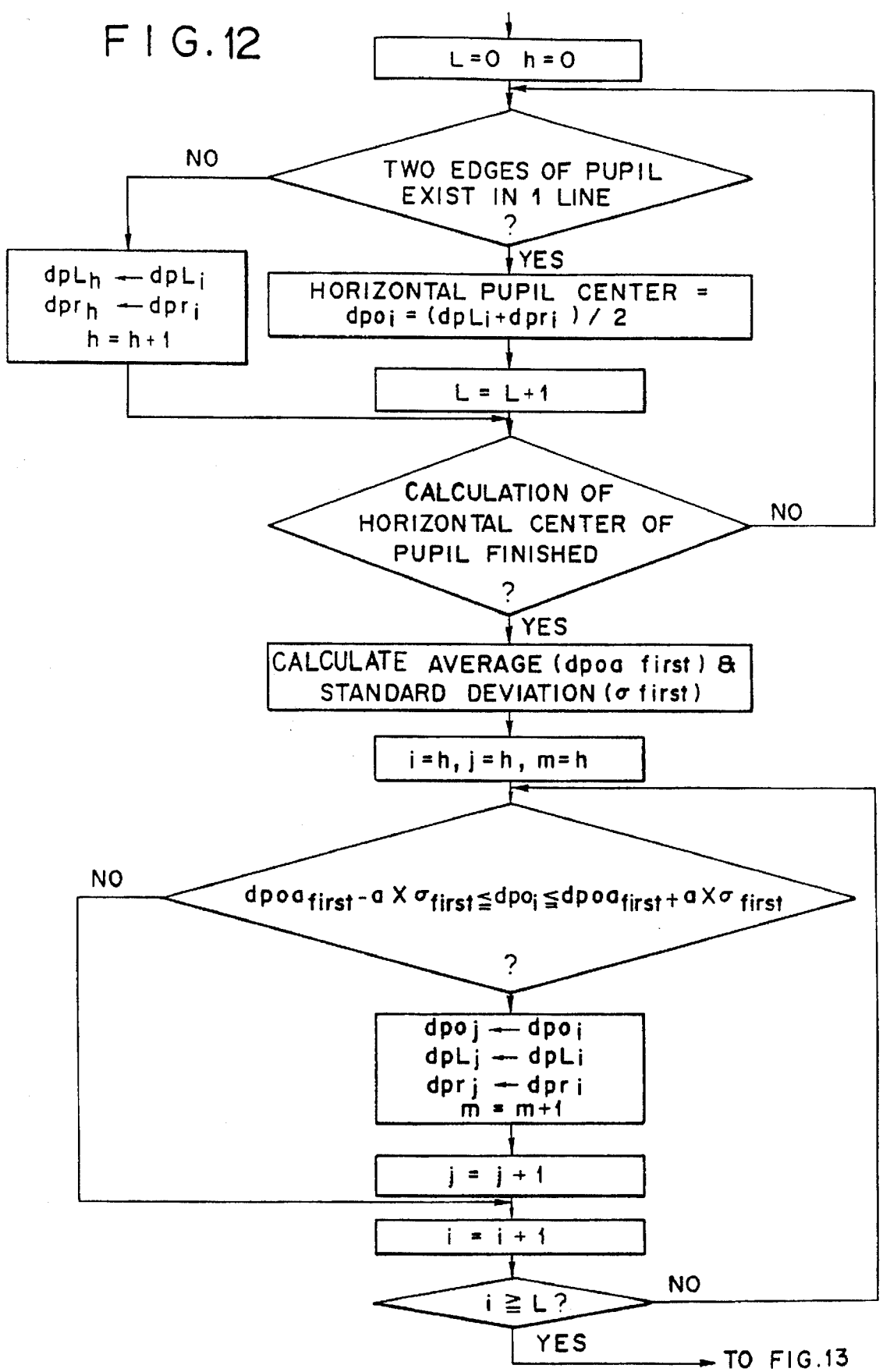
FIG. 12 is a flow chart showing a pupil edge selection routine.
Figure 13:
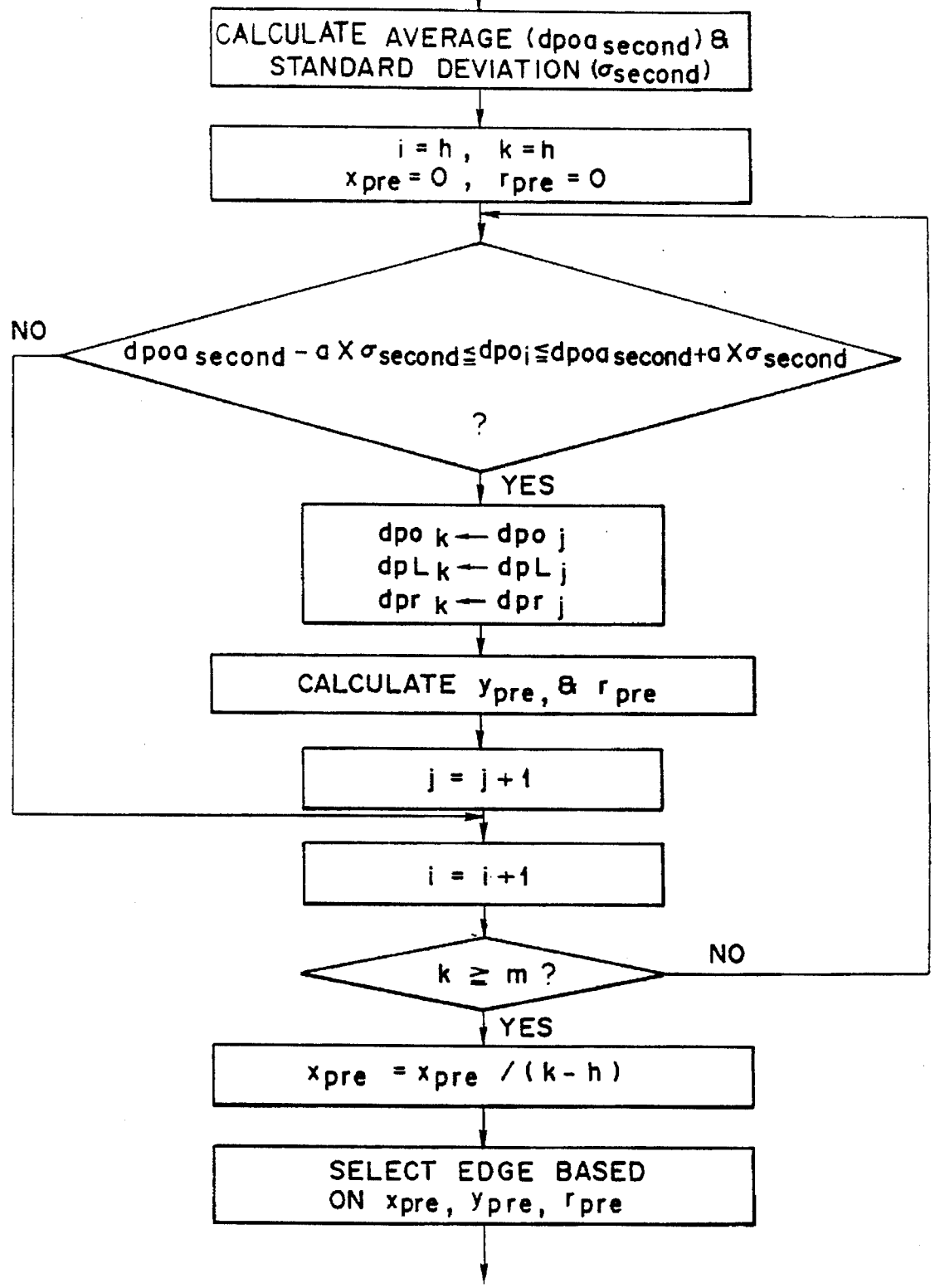
FIG. 13 is a flow chart showing the pupil edge selection routine.

Upon completion of the horizontal and vertical pupil edge extraction operations, an operation for finally calculating the pupil center Dc ($x_0$, $y_0$) from the extracted information and/or selecting information to be used upon calculation of the pupil center Dc ($x_0$, $y_0$) are performed. This operation is performed as follows. FIGS. 12 and 13 are flow charts showing this operation sequence.

The M.P.U. obtains horizontal pupil centers $dpo_i$ in units of lines using information of the horizontal pupil edge positions obtained in the above operations, and at the same time, counts the number L of obtained $dpo_i$.

In this case, information corresponding to only one pupil edge on a single line is not used in calculations of an average value and a standard deviation. However, when this information falls within a range determined by a presumed pupil center and a presumed pupil diameter (to be described later), it is determined to be effective data, and is used in the subsequent calculations. An average value $dpoa_{first}$ and a standard deviation $\sigma_{first}$ are calculated using the horizontal pupil central positions $dpo_i$ obtained as described above in the same manner as in the first embodiment.

Using these two values, a range of effective horizontal pupil centers $dpo_i$ is defined as $dpoa_{first} - a \times \sigma_{first} \leq dpo_i \leq dpoa_{first} + a \times \sigma_{first}$.

In this case, a is an arbitrary constant. When the range is defined, it is checked if each $dpo_i$ falls within this range. If it is determined that given $dpo_i$ falls within this range, $dpo_i$ and two horizontal pupil edge positions $dpL_i$ and $dpr_i$ used in the calculation of $dpo_i$ are stored as $dpo_j$, $dpL_j$, and $dpr_j$. At the same time, the number m of selected $dpo_i$ is counted. This operation is repeated by the number (L–h) of obtained $dpo_i$.

Furthermore, the same processing is performed again using the selected $dpo_j$, $dpL_j$, and $dpr_j$. More specifically, an average value $dpoa_{second}$ and a standard deviation $\sigma_{second}$ are calculated using the selected horizontal pupil centers $dpo_j$ to define a range $dpoa_{second} - a \times \sigma_{second} \leq dpo_j dpoa_{second} + a \times \sigma_{second}$, and it is checked if $dpo_j$ falls within this range.

If it is determined that $dpo_j$ falls within this range, two horizontal pupil edge positions $dpL_j$ and $dpr_j$ are stored as $dpL_K$ and $dpr_K$. Then, $dpo_j$ at that time is added to a counter for obtaining a presumed horizontal pupil center $x_{pre}$. Also, a presumed vertical pupil center $y_{pre}$ and a presumed pupil diameter $r_{pre}$ are calculated in the same manner as in the first embodiment.

More specifically, the absolute value of a difference between $dpL_j$ and $dpr_j$ is calculated, and is compared with a presumed pupil diameter $r_{pre}$ (an initial value of $r_{pre}$ is zero) detected so far. If $abs(dpL_j - dpr_j) > r_{pre}$ is satisfied, $abs(dpL_j - dpr_j)$ is adopted as new $r_{pre}$. At the same time, the vertical coordinate at that time is stored as a presumed vertical pupil center $y_{pre}$. This operation is repeated by the number (m–h) of selected $dpo_j$.

After the control exits the above-mentioned loop, the content of the counter for obtaining $x_{pre}$ is divided by the number (k–h) of $dpo_j$ falling within the range ($dpoa_{second} - a \times \sigma_{second} \leq dpo_j \leq dpoa_{second} + a \times \sigma_{second}$) defined by the average value $dpoa_{second}$ and the standard deviation $\sigma_{second}$, thus obtaining a presumed horizontal pupil center $x_{pre}$.

Then, edge information selection executed using the presumed pupil central positions $x_{pre}$ and $y_{pre}$ and the presumed pupil diameter $r_{pre}$ obtained as described above will be described below (see FIG. 6). The M.P.U. selects information falling within ranges of $x_{pre} \pm (r_{pre}/2 + \alpha_1)$ and $y_{pre} \pm (r_{pre}/2 + \alpha_2)$.

When extraction and selection of the horizontal and vertical pupil edges are ended, as described above, a pupil center Dc ($x_0$, $y_0$) is calculated using the selected information. As an effective calculation method, a pupil may be assumed to be a circle, and a method of least squares may be used.

As described above, in the first and second embodiments, a large number of positions on a pupil ring are obtained using an image sensor (two-dimensional solid-state image pickup element), an average value of pupil edges on a single horizontal (or vertical) line, i.e., an average value and a standard deviation of a large number of horizontal (or vertical) pupil centers are calculated, and information falling within a range defined by these two values is determined to be effective information to obtain a pupil center. In this manner, the conventional problems can be solved, and even when a ghost is generated due to eyeglasses or a pupil edge is eclipsed by an eyelid, the pupil center can be detected with high precision.

In the first and second embodiments, a large number of positions on a pupil ring are obtained using an image sensor (two-dimensional solid-state image pickup element), horizontal and vertical pupil central positions and a pupil diameter of a photographer are presumed from the obtained information, and only information falling within a range defined by these presumed values is determined to be effective information to obtain a pupil center. In this manner, the conventional problems can be solved, and even when a ghost is generated due to eyeglasses or a pupil edge is eclipsed by an eyelid, the pupil center can be detected with high precision.

A pupil ring detection method of the present invention will be described below.

In the pupil ring detection method of the present invention, after signals are read, maximum and minimum values of the read signals are obtained, a calculation is started from a calculation start point defined based on the output from a Purkinje image position detection means, and a position which satisfies the following conditions is determined as a boundary between an iris and a pupil:

(3-a) the output signal continuously increases or decreases over several pixels or more (three to five pixels);

(3-b) the start point of the increase or the end point of the decrease, i.e., the minimum value of a slope is equal to the previously obtained minimum value of the signals;

(3-c) the end point of the increase or the end point of the decrease, i.e., the maximum value of the slope is smaller than an average of the previously obtained maximum and minimum values of the signals; and (3-d) the start and end points of the increase and decrease are not present near a Purkinje image.

In this manner, the following conventional problems can be solved, and the boundary between the pupil and the iris can be detected regardless of the state of the eyeball.

(A) A recognition error is caused by a pattern of a noise iris included in the signals, a change in signal due to non-uniform eyelash illumination, and a ghost generated by an edge of a contact lens or eyeglasses.

(B) When a Purkinje image is present outside the pupil, the Purkinje image is erroneously recognized as the boundary between the pupil and the iris.

(C) When the pupil is eclipsed by an eyelid in detection in the vertical direction, the boundary between the pupil and the eyelid is erroneously recognized as the boundary between the pupil and the iris.

The first embodiment of the pupil ring detection method of the present invention will be described below.

Figure 14:
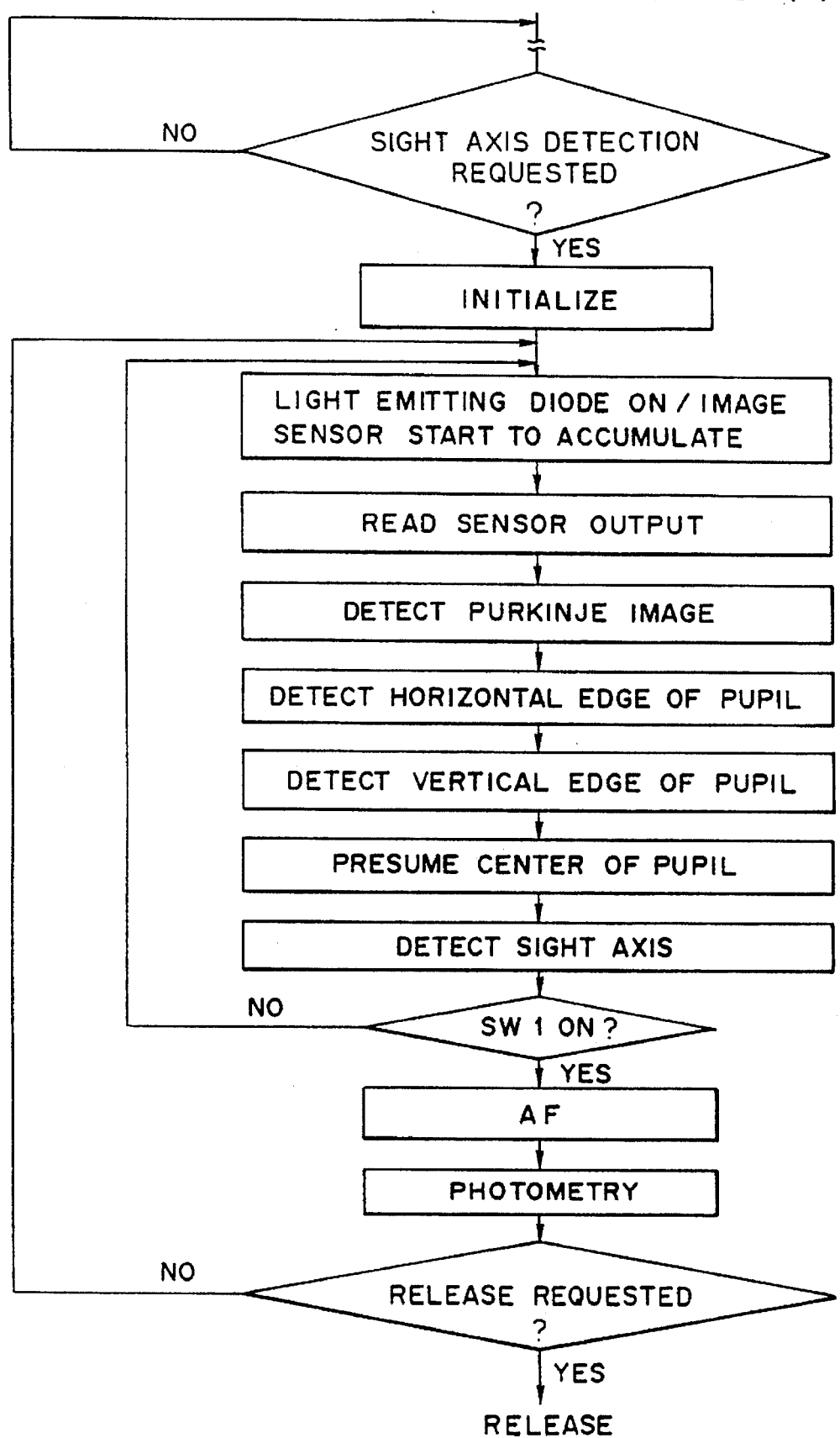
FIG. 14 is a flow chart showing another sight axis detection routine.

When a main switch (not shown) of the camera is turned on to request the start of sight axis detection, the control of the M.P.U. 1 enters a sight axis detection routine. FIG. 14 is a flow chart showing this routine.

When the control newly enters the sight axis detection routine, initialization processing is performed to initialize all variables associated with sight axis detection. Upon reception of information of the posture position (vertical or horizontal position) of the camera at that time from the position sensor 6, the light emission control circuit 5 selects infrared light-emitting diodes (iRED) 7a to be driven. At the same time, the M.P.U. 1 supplies, via the interface circuit 3, an integration signal to the driving circuit 4b and a light emission control signal synchronous with the integration signal to the light emission control circuit 5. With these signals, the accumulation operation of the image sensor 4a and the light emission operation of the infrared light-emitting diodes 7a corresponding to the camera position at that time are synchronously performed.

An image of the front eye part of the eyeball corresponding to a Purkinje image formed on the image sensor 4a is read through the interface circuit 3. By processing the read image, a position P of the Purkinje image, a plurality of pupil ring portions (so-called pupil edges) $D_i$, and a pupil center Dc ($x_0$, $y_0$) are detected. Then, horizontal and vertical rotational angles $\theta_H$ and $\theta_V$ of the eyeball are calculated from the detected values. After the rotational angles of the eyeball are calculated, a personal difference correction such as a sight axis correction is performed to obtain a view point, on the focusing screen, of the photographer.

The above-mentioned operations are repeated until a release button of the camera is depressed to its half-stroke position to turn on a switch SW1. When the switch SW1 is turned on, the view point information, on the focusing screen, of the photographer obtained, as described above, is fed back to various operations such as an AF operation, a photometry operation, and the like of the camera. For example, in the AF operation, the M.P.U. 1 performs an AF calculation using a signal of a portion, corresponding to the view point, of the AF sensor 8 to obtain a lens driving amount for achieving an in-focus state. Thereafter, the M.P.U. 1 performs focus adjustment by controlling the lens driver unit 9.

Also, in the photometry operation, the M.P.U. 1 calculates exposure constants (a shutter speed, an aperture value, and the like) according to a designated photographing mode on the basis of a signal of a portion, corresponding to the view point, of the photometry sensor 10. When a release request is issued, the M.P.U. executes a series of release operations such as an operation for driving the aperture to the calculated aperture value, an operation for opening/closing a shutter, a film wind-up operation, and the like.

Figure 15:
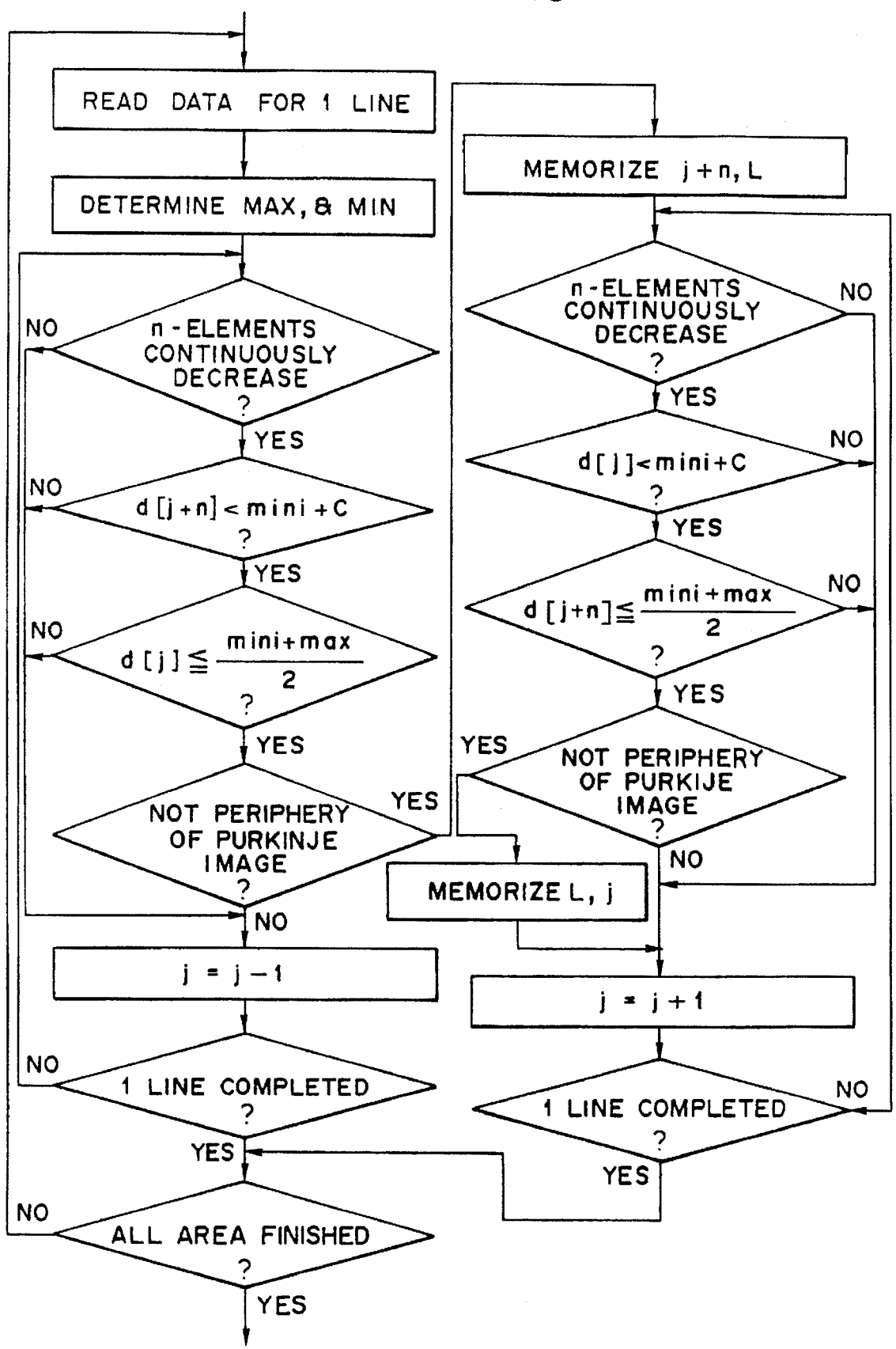
FIG. 15 is a flow chart showing the first embodiment of a pupil ring portion position detection routine.

A method of obtaining pupil ring portion (pupil edge) positions $D_i$ will be described below. FIG. 15 is a flow chart showing the method of obtaining pupil edge positions $D_i$.

As described above, when the control enters the sight axis detection routine, the memory content is initialized, the infrared light-emitting diodes (iRED) are caused to emit light, signal outputs from the sensor are read, and so on. Based on the read output signals, Purkinje images are detected, and the detection result is stored in the memory.

When the control enters a horizontal pupil edge detection routine, data for one line is read, and the positions of pupil edges are detected for the read line. A maximum value (max) and a minimum value (mini) are obtained from the read 1-line data. These two values are the maximum and minimum values of the line read at that time, and do not always coincide with maximum and minimum values of the entire image.

The M.P.U. checks if the output signal continuously decreases over n pixels.

More specifically, the M.P.U. checks if the following relation is satisfied:

$$d_{[j]} > d_{[j+1]} > d_{[j+2]} > \ldots > d_{[j+n-1]} > d_{[j+n]}$$

Then, the M.P.U. checks if $d_{[j+n]}$ corresponding to the minimum value of the slope is substantially equal to the minimum value (mini) of the read line, i.e., if $d_{[j+n]} \leq \text{mini} + c$ is satisfied.

Furthermore, the M.P.U. checks if $d_{[j]}$ corresponding to the maximum value of the slope is smaller than an average value (mini+max)/2 of the maximum and minimum values of the read line. Thus, a falling slope from the iris where the signal intensity is equal to or smaller than the average value of the maximum value (max) and the minimum value (mini) to the pupil where the signal intensity is substantially equal to the minimum value can be detected.

Furthermore, whether or not this point is present near the periphery of the previously obtained Purkinje image is checked to prevent a detection error due to the influence of the Purkinje image. A position satisfying the above-mentioned four conditions is determined to be a pupil edge, and a line number L and a pixel number (i+n) of the position are stored in the memory as pupil edge information.

Thereafter, the M.P.U. enters a routine for detecting an opposite pupil edge. Conversely, when the above-mentioned conditions are not satisfied, the same processing is performed for a neighboring pixel.

In the routine for detecting the opposite pupil edge, the same processing is performed. More specifically, if a position satisfies the following four conditions, the position is determined to be a pupil edge, its line number n and a pixel number (j) are stored in the memory as pupil edge information, and processing is then performed for a neighboring pixel.

(3-1) The output signal continuously increases over n pixels.

(3-2) $d_{[j]}$ corresponding to the minimum value of a slope is substantially equal to the minimum value (mini).

(3-3) $d_{[j+n]}$ corresponding to the maximum value of the slope is equal to or smaller than an average value of the maximum value (max) and the minimum value (mini).

(3-4) The corresponding point is not present near the periphery of the previously obtained Purkinje image.

Conversely, if the conditions are not satisfied, the processing is also performed for a neighboring pixel. With this processing, the memory stores position information of a finally found pupil edge, i.e., the outermost edge. The previously obtained edge is one found for the first time, and also corresponds to the outermost pupil edge (see FIG. 5).

The above-mentioned processing is performed over the entire frame in units of lines to obtain a plurality of pupil edge positions.

Upon completion of the processing for the entire frame, the control enters a vertical pupil edge detection routine. In this routine, the same processing as described above is performed to obtain pupil edges.

In this routine, however, since the maximum and minimum values of signals on the entire frame have already been determined in the horizontal pupil edge detection routine, these values are used in the calculation of this routine, and a calculation for obtaining the maximum and minimum values is omitted.

Upon completion of both the horizontal and vertical pupil edge extraction operations, the pupil center Dc ($x_0$, $y_0$) is finally calculated from these pieces of information. In this case, the pupil may be assumed to be a circle, and a method of least squares may be used as an effective method.

The second embodiment of the pupil ring detection method of the present invention will be described below.

This embodiment is characterized in that the start and end points of a slope of a pupil edge are obtained, and an average value of these points is determined to be a pupil edge position. The arrangement of this embodiment is substantially the same as that shown in FIG. 1. The operation flow chart of this embodiment is substantially the same as that shown in FIG. 14.

As in the first embodiment of the pupil ring detection method, when the start of sight axis detection is requested, and the control newly enters the sight axis detection routine, initialization processing is performed to initialize all variables associated with sight axis detection. Upon reception of information of the posture position (vertical or horizontal position) of the camera at that time from the position sensor 6, the light emission control circuit 5 selects infrared light-emitting diodes (iRED) 7a to be driven. At the same time, the M.P.U. 1 supplies, via the interface circuit 3, an integration signal to the driving circuit 4b and a light emission control signal synchronous with the integration signal to the light emission control circuit 5. With these signals, the accumulation operation of the image sensor 4a, and the light emission operation of the iREDs corresponding to the camera posture are synchronously performed.

An image of the front eye part of the eyeball corresponding to a Purkinje image formed on the image sensor 4a is read through the interface circuit 3. By processing the read image, a position P of the Purkinje image and/or a plurality of pupil ring portions (so-called pupil edges) $D_i$ are detected. Horizontal and vertical rotational angles $\theta_H$ and $\theta_V$ of the eyeball are calculated using the detected values. After the rotational angles of the eyeball are calculated, a personal difference correction such as a sight axis correction is performed to obtain a view point, on the focusing screen, of the photographer.

The above-mentioned operations are repeated until a release button of the camera is depressed to its half-stroke position to turn on a switch SW1. When the switch SW1 is turned on, the view point information, on the focusing screen, of the photographer obtained, as described above, is fed back to various operations such as an AF operation, a photometry operation, and the like of the camera. For example, in the AF operation, the M.P.U. 1 performs an AF calculation using a signal of a portion, corresponding to the view point, of the AF sensor 8 to obtain a lens driving amount for achieving an in-focus state. Thereafter, the M.P.U. 1 performs focus adjustment by controlling the lens driver unit 9.

Also, in the photometry operation, the M.P.U. 1 calculates exposure constants (a shutter speed, an aperture value, and the like) according to a designated photographing mode on the basis of a signal of a portion, corresponding to the view point, of the photometry sensor 10. When a release request is issued, the M.P.U. executes a series of release operations such as an operation for driving the aperture to the calculated aperture value, an operation for opening/closing a shutter, a film wind-up operation, and the like.

Figure 16:
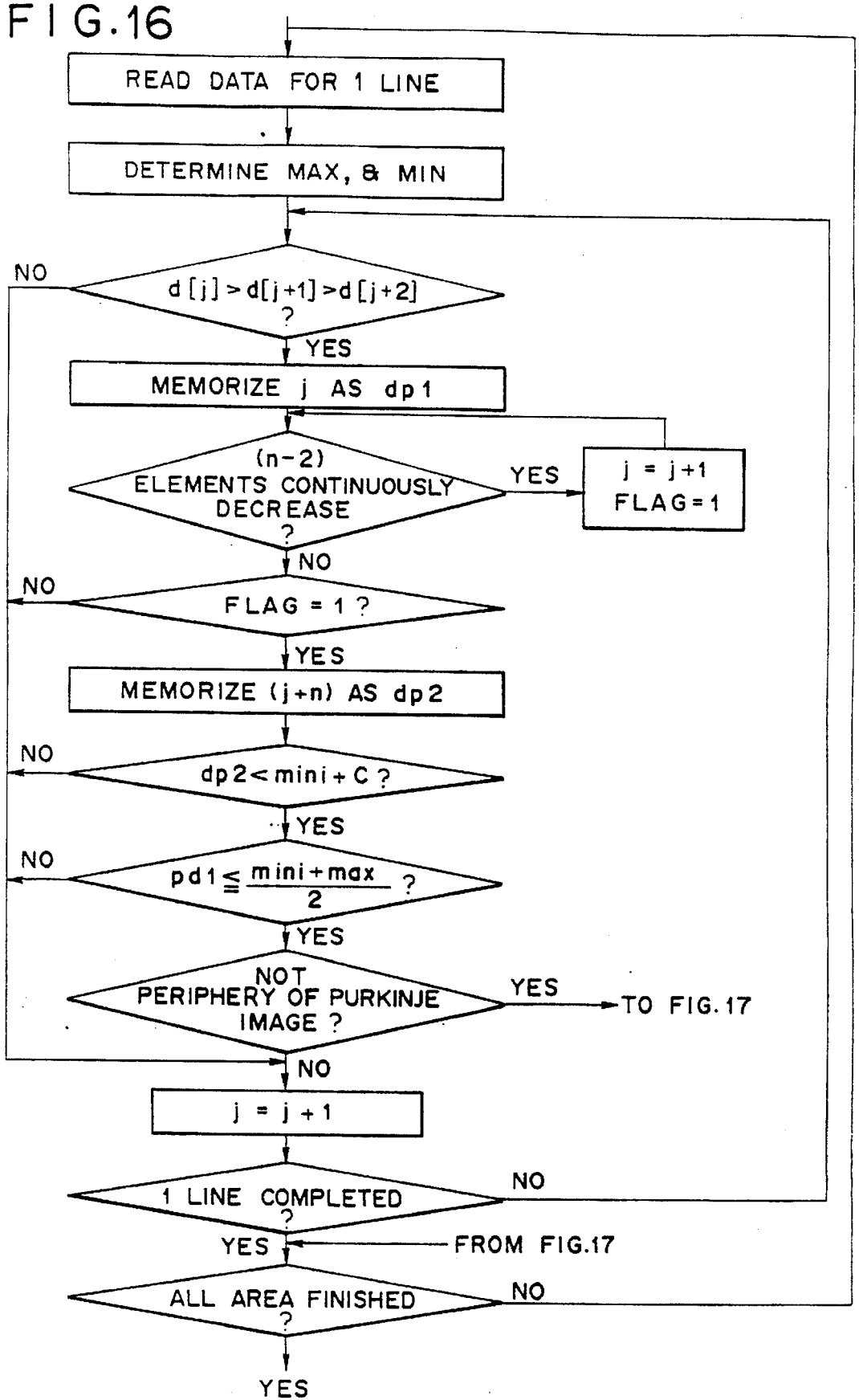
FIG. 16 is a flow chart showing the second embodiment of a pupil ring portion position detection routine.
Figure 17:
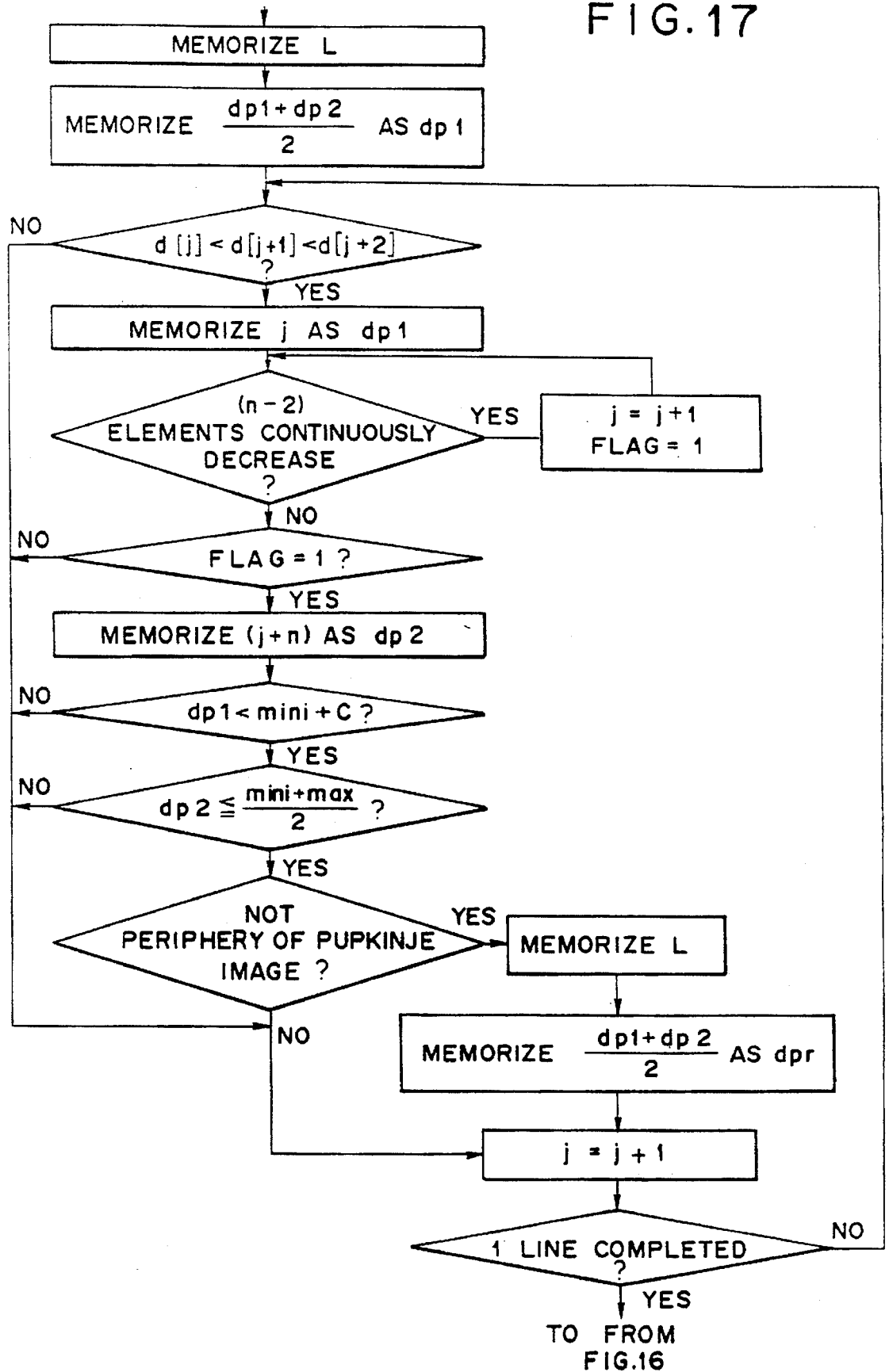
FIG. 17 is a flow chart showing the second embodiment of the pupil ring portion position detection routine.

A routine for calculating pupil edge positions $D_i$ will be described in detail below. FIGS. 16 and 17 are flow charts showing this routine.

As described above, when the control enters the sight axis detection routine, the memory content is initialized, the infrared light-emitting diodes (iRED) are caused to emit light, signal outputs from the sensor are read, and so on. Based on the read output signals, Purkinje images are detected, and the detection result is stored in the memory.

When the control enters a horizontal pupil edge detection routine, data for one line is read, and the positions of pupil edges for this line are detected. A maximum value (max) and a minimum value (mini) are obtained from the read 1-line data. These two values are the maximum and minimum values of the line read at that time, and do not always coincide with maximum and minimum values of the entire image.

Figure 5:
FIG. 5 is a chart for explaining a signal obtained by an image sensor.

The M.P.U. then checks if the output signal continuously decreases over n pixels. More specifically, as shown in FIG. 5, the M.P.U. obtains a point which satisfies the following relation, i.e., the start point of the decrease, and stores the point in the memory as dp1:

$$d_{[j]} > d_{[j+1]} > d_{[j+2]}$$

Then, the M.P.U. searches points satisfying the following relation, i.e., points where the output signal continuously decreases over (n–2) pixels:

$$d_{[j+2]} > d_{[j+3]} > \ldots d_{[j+n]}$$

Since (n–2) pixels are set, a position where the output signal continuously decreases over n pixels is obtained in combination with the above condition.

In the processing associated with the second condition, j is incremented while the condition is satisfied; when the condition is not satisfied, the control exits the loop, and a position at that time is stored in the memory as dp2. However, when the control exits the loop without satisfying the conditions any time, no data is stored in the memory, and the processing is performed for a neighboring pixel.

It is then checked if dp2 corresponding to the minimum value of a slope is substantially equal to the minimum value (mini) of the read line, and it is also checked if dp1 corresponding to the maximum value of the slope is smaller than an average value (mini+max)/2 of the maximum and minimum values of the read line. Thus, a falling slope from the iris where the signal intensity is equal to or smaller than the average value of the maximum value and the minimum value to the pupil where the signal intensity is substantially equal to the minimum value can be detected. Furthermore, whether or not dp1 and dp2 are present near the periphery of the previously obtained Purkinje image is checked to prevent a detection error caused by the influence of the Purkinje image.

A position satisfying the above-mentioned four conditions is determined to be a pupil edge, and an average value of dp1 and dp2 is stored as pupil edge information (dpL) together with its line number L. When a position satisfying the four conditions is found, the information of the position is stored in the memory, and thereafter, the control enters a routine for detecting an opposite pupil edge; otherwise, the same processing is performed for a neighboring pixel.

In the routine for detecting the opposite pupil edge, the same processing is performed. More specifically, when a certain position satisfies the following four conditions, the position is determined to be as a pupil edge, dpr (=(dp1+dp2)/2) and a line number L are stored in the memory as the information of the position, and thereafter, the processing is performed for a neighboring pixel.

(4-1) A point satisfying $d_{[j]} < d_{[j+1]} > d_{[j+2]}$ corresponding to the start point of an increase and a point satisfying $d_{[j+2]} < d_{[j+3]} < \ldots < d_{[j+n]}$ corresponding to the end point of the increase are present.

(4-2) dp1 $(=d_{[j]})$ corresponding to the minimum value of a slope is substantially equal to the minimum value (mini).

(4-3) dp2 $(=d_{[j+n]})$ corresponding to the maximum value of the slope is equal to or smaller than an average value of the maximum value (max) and the minimum value (mini).

(4-4) The corresponding point is not present near the periphery of the previously obtained Purkinje image.

The above-mentioned processing is performed over the entire frame in units of lines to obtain a plurality of pupil edge positions.

Upon completion of the processing for the entire frame, the control enters a vertical pupil edge detection routine. In this routine, the same processing as described above is performed to obtain pupil edges. In this routine, however, since the maximum and minimum values of signals on the entire frame have already been determined in the horizontal pupil edge detection routine, these values are used in the calculation of this routine, and a calculation for obtaining the maximum and minimum values is omitted.

Upon completion of the horizontal and vertical pupil edge extraction operations, a pupil center Dc $(x_0, y_0)$ is calculated using these pieces of information. In this case, the pupil may be assumed to be a circle, and a method of least squares may be used as an effective method.

As described above, in the first and second embodiments of the pupil ring detection method of the present invention, a position satisfying the following four conditions is determined to be a pupil edge, thereby solving the conventional problems, and extracting pupil edges with high precision.

(4-a) The output signal continuously increases or decreases over n pixels or more.

(4-b) The minimum value of a slope is substantially equal to the minimum value of all signals.

(4-c) The maximum value of the slope is equal to or smaller than the average value of the maximum and minimum values of all signals.

(4-d) The corresponding point is not present near the periphery of the previously obtained Purkinje image.

According to the present invention, as described above, there can be provided a pupil center detection method and a pupil ring portion detection method which can detect the pupil center and pupil edges with high precision, i.e., the sight axis of the eyeball with high precision by properly processing signals obtained from an image sensor (two-dimensional image pickup element) on the basis of specific points based on light beams reflected by an eyeball.

What is claimed is:

1. A method of illuminating an eyeball with illuminating means to use an apparatus for optically receiving an image of the eyeball, a Purkinje image of which is generated by the illumination, with a light-receiving device to detect a pupil edge of the eyeball, the method comprising:

a first step of detecting the position of the Purkinje image from signals of the image of the eyeball outputted by the light-receiving device;

a second step of determining a detection starting position for detecting a pupil edge of the eyeball based on the position of the Purkinje image detected by said first step, wherein said second step changes the detection starting position according to the position of the Purkinje image detected in said first step; and a third step of detecting the pupil edge from said detection starting position determined by said second step.

2. A method according to claim 1, wherein the illuminating means generate a plurality of Purkinje images of the eyeball by illuminating the eyeball with a plurality of light sources to detect the coordinates of the positions of the plurality of Purkinje images in said first step to determine the detection starting position based on the position of coordinates obtained by averaging the coordinates of the positions of the plurality of Purkinje images in said second step.

3. A method according to claim 1, wherein the illuminating means generates a plurality of Purkinje images of the eyeball by illuminating the eyeball with a plurality of light sources to detect the coordinates of positions of the plurality of Purkinje images in said first step to determine the detection starting position based on at least one of the coordinates of the position of a Purkinje image among the plurality of Purkinje images in said second step.

4. A device for detecting a pupil edge comprising:

illuminating means for illuminating an eyeball with light;

light-receiving means for optically receiving an image of the eyeball the Purkinje image of which is generated by said illuminating means;

pupil edge detecting means for detecting a pupil edge of the eyeball from signals of the image of the eyeball outputted by said light receiving means; and Purkinje image detecting means for detecting a position of the Purkinje image from signals of the image of the eyeball outputted by said light-receiving means, wherein said pupil edge detecting means changes its starting position of operation for detecting the pupil edge based on the position of the Purkinje image detected by said Purkinje image detecting means.

5. A device according to claim 4, wherein said illuminating means illuminates the eyeball with a plurality of light sources to generate a plurality of Purkinje images of the eyeball so that said device detects the coordinates of the positions of the plurality of Purkinje images by the detection of the Purkinje image by said Purkinje image detecting means and so that said pupil edge detecting means determines the starting point of operation of the detection based on the position of coordinates obtained by averaging the coordinates of the positions of the plurality of Purkinje images.

6. A device according to claim 4, wherein said illuminating means illuminates the eyeball with a plurality of light sources to generate a plurality of Purkinje images of the eyeball, wherein said Purkinje image detecting means detects the coordinates of positions of the plurality of Purkinje images, wherein said pupil edge detecting means determines the starting position of, operation based on coordinates of the position of at least one of the Purkinje images among coordinates of the positions of the plurality of Purkinje images.

7. A device according to claims 4, wherein said illuminating means illuminate the eyeball with a pair of light sources to generate a pair of Purkinje images of said eyeball, and wherein said pupil edge detecting means changes the starting position of operation of detection for detecting the pupil edge based on the position of a middle point between a pair of Purkinje images.

8. A device according to claim 4, wherein said pupil edge detecting means ends the operation of detection at the time when the said pupil edge detecting means detects the pupil edge.

* * * * *

UNITED STATES PATENT AND TRADEMARK OFFICE
CERTIFICATE OF CORRECTION

PATENT NO. : 5,657,110
DATED : August 12, 1997
INVENTOR(S) : KAZUKI KONISHI

It is certified that error appears in the above-indentified patent and that said Letters Patent is hereby corrected as shown below:

SHEET 17 OF THE DRAWINGS

Figure 17, "PUPKINJE" should read --PURKINJE--.

COLUMN 3

Line 34, "be" should read --beam--.

COLUMN 6

Line 43, "sub mirror" should read --sub-mirror--.

COLUMN 22

Line 18, "of," should read --of--.

Signed and Sealed this

Seventeenth Day of March, 1998

Attest:

BRUCE LEHMAN

Attesting Officer     Commissioner of Patents and Trademarks